United States Patent [19]
Inoue et al.

[11] Patent Number: 6,153,072
[45] Date of Patent: Nov. 28, 2000

[54] GAS SENSOR, GAS SENSOR SYSTEM USING THE SAME, AND METHOD OF MANUFACTURING A GAS SENSOR

[75] Inventors: Ryuji Inoue, Gifu; Shoji Kitanoya, Aichi; Kenji Kato, Aichi; Tomohiro Fuma, Aichi; Takafumi Oshima, Aichi, all of Japan

[73] Assignee: NGK Spark Plug Co., Ltd., Nagoya, Japan

[21] Appl. No.: 09/150,295

[22] Filed: Sep. 9, 1998

[30] Foreign Application Priority Data

Sep. 9, 1997 [JP] Japan .................................. 9-262732
Jul. 28, 1998 [JP] Japan ................................. 10-213341

[51] Int. Cl.[7] ....................... G01N 27/407; G01N 27/419
[52] U.S. Cl. ........................... 204/425; 204/426; 205/787
[58] Field of Search .................................. 204/425, 426, 204/427, 424; 205/784.5, 787

[56] References Cited

U.S. PATENT DOCUMENTS

| | | | |
|---|---|---|---|
| 4,722,779 | 2/1988 | Yamada et al. | 204/425 |
| 5,763,763 | 6/1998 | Kato et al. | 73/23.2 |
| 5,879,525 | 3/1999 | Kato | 204/424 |

FOREIGN PATENT DOCUMENTS

| | | |
|---|---|---|
| 0 050 944 A1 | 9/1982 | European Pat. Off. . |
| 0 678 740 A1 | 10/1995 | European Pat. Off. . |
| 0 731 351 A2 | 9/1996 | European Pat. Off. . |
| 0 797 094 A2 | 9/1997 | European Pat. Off. . |
| 0 851 225 A2 | 7/1998 | European Pat. Off. . |

OTHER PUBLICATIONS

David M. Haaland, Noncatalytic Electrodes for Solid–Electrolyte Oxygen Sensors, J. Electrochemical Soc., pp. 796–804, Apr. 1980.

Primary Examiner—Robert J. Warden, Sr.
Assistant Examiner—Kaj K. Olsen
Attorney, Agent, or Firm—Sughrue, Mion, Zinn, Macpeak & Seas, PLLC

[57] ABSTRACT

A gas sensor 1 including a first processing space 9; a first gas passage 11; a second processing space 10; a second gas passage 13; an oxygen concentration detection element 4; a first oxygen pumping element 3 adapted to reduce the oxygen concentration of exhaust gas introduced into the first processing space 9 within a range such that a water vapor contained in the measurement gas is not substantially decomposed; an oxygen catalyst section 16; and a combustible gas component concentration information generation/output section 5. Also disclosed is a gas sensor system including the above gas sensor and first oxygen pumping operation control means for adjusting the oxygen concentration of the measurement gas introduced into the first processing space within a range such that water vapor contained in the measuring gas is not substantially decomposed.

48 Claims, 25 Drawing Sheets

GAS SENSOR, GAS SENSOR SYSTEM USING THE SAME, AND METHOD OF MANUFACTURING A GAS SENSOR

FIELD OF THE INVENTION

The present invention relates to a gas sensor, a gas sensor system using the same, and a method of manufacturing the gas sensor.

BACKGROUND OF THE INVENTION

Resistance-type sensors are known for measuring the concentration of a combustible gas component such as hydrocarbon (HC) or CO contained in the exhaust gas of an automobile or the like. For example, an oxide semiconductor (n-type) such as $SnO_2$ or the like is used as a sensing element for measuring the concentration of a combustible component such as HC or CO. Specifically, oxygen in the atmosphere adsorbs onto the sensing element through an effect induced by negative charges. When the atmosphere contains a combustible component such as HC or CO, the combustible gas component undergoes a combustion reaction with the adsorbed oxygen, thereby causing oxygen to be desorbed from the sensing element. Because a change in electric resistance of the sensing element associated with the oxygen desorption depends on the combustible gas component concentration of the atmosphere, the combustible component concentration of the atmosphere can be obtained by measuring the change in electric resistance. However, such a resistance-type sensor has a drawback in that the output from the sensing element formed of an oxide semiconductor is likely to vary depending on the concentration of oxygen or water vapor contained in the exhaust gas. Accordingly, even when the combustible gas component remains unchanged, the detection output value can vary depending on, for example, the oxygen concentration of the exhaust gas.

In order to solve the above problem, an apparatus for measuring a combustible gas component concentration having the following structure is disclosed in Japanese Patent Application Laid-Open No. 8-247995. In this apparatus, the sensing element has two processing zones. An exhaust gas is introduced into a first processing zone via a first diffusion-controlling means. Oxygen is pumped out from the first processing zone by means of a first oxygen pumping element so as to reduce the oxygen concentration of the first processing zone to a low value at which combustible gas components are not substantially burned. Next, the gas having the thus-reduced oxygen concentration is introduced into a second processing zone via a second diffusion-controlling means. Oxygen is pumped into the second processing zone by means of a second oxygen pumping element so as to burn the combustible gas component. The combustible gas component concentration is determined based on a value of current flowing through or voltage developed across the second oxygen pumping element. According to the above-described patent publication, the above-described structure enables the concentration of the combustible gas component contained in a measurement gas to be advantageously measured without being affected by the oxygen concentration.

In the above disclosed apparatus, the oxygen concentration of the exhaust gas introduced into the first processing zone is reduced by means of the first oxygen pumping element to "a low value at which a combustible gas component is not substantially burned". According to this publication, the low value is not higher than $10^{-14}$ atm, preferably not higher than $10^{-16}$ atm, and is normally about $10^{-20}$ atm. However, when the oxygen concentration of the first processing zone is set at such a low value, the following problem arises related to accuracy in measuring the combustible gas component concentration.

Specifically, an exhaust gas generally contains a fair amount of water vapor in addition to combustible gas components such as hydrocarbon, carbon monoxide and hydrogen. Generally, the amount of water vapor varies according to the operating conditions of an internal combustion engine. According to studies conducted by the present inventors, when the oxygen concentration of such an exhaust gas is reduced to the above-mentioned value, a portion of the water vapor is decomposed into hydrogen and oxygen. The thus-generated oxygen is pumped out from the first processing zone by means of the first oxygen pumping element, whereas the thus-generated hydrogen is not pumped out, but introduced into the second processing zone where the hydrogen induces combustion. In such a state, hydrogen that is originally contained in a gas to be measured (also referred to as an object gas) and hydrogen derived from water vapor cannot be distinguished from each other, so that accuracy in measuring the hydrogen concentration is adversely affected. In addition, when the object gas mainly contains hydrocarbon as a combustible gas component and does not contain much hydrogen, combustion of hydrogen generated by decomposition of water vapor significantly affects accuracy in measuring hydrocarbon concentration. Notably, the measurement examples disclosed in the above patent publication were all conducted under conditions such that the water vapor concentration of the object gas was constant, and did not take into account the influence of a variation in water vapor concentration when measuring a combustible gas component concentration.

As disclosed in the above patent publication, a proton pump may be additionally used in order to pump out the thus-generated hydrogen from the first processing zone, so that only HC is selectively burned to thereby improve the measurement accuracy. However, this method merely employs the proton pump as a means of last resort for coping with hydrogen generation associated with the decomposition of water vapor. Addition of the proton pump makes the sensor structure and a sensor control mechanism complex, causing an increase in the apparatus cost. Furthermore, residual hydrogen which the proton pump has failed to remove may induce a measurement error.

Also, the following problem is encountered. With the recent tendency to tighten exhaust gas regulations for air pollution control, internal combustion engines such as gasoline engines, diesel engines and like engines tend to shift to a lean-burn operation in order to suppress generation of HC associated with incomplete combustion. An exhaust gas produced under lean-burn conditions has an oxygen concentration higher than that produced under stoichiometric or rich conditions. When the above-described conventional apparatus is applied to such an exhaust gas, an oxygen pumping element is significantly burdened in order to reduce the oxygen concentration to the above-mentioned low value. As a result, the service life of the oxygen pumping element is shortened. Furthermore, since the operating power of the oxygen pumping element must be increased, a high output peripheral control circuit must also be used which in turn increases the apparatus cost.

SUMMARY OF THE INVENTION

It is therefore an object of the present invention to provide a gas sensor and a method of manufacturing the gas sensor in which accuracy in measuring a combustible gas component concentration is less susceptible to decomposition of water vapor and which is suitably applicable to lean-burn conditions, as well as to provide a gas sensor system using the gas sensor.

The above object of the present invention is achieved by providing a gas sensor having the following characteristic features.

(1) First processing space: A first processing space is provided which is isolated from the surrounding environment. A gas to be measured (hereinafter referred to as a "measurement gas") is introduced into the first processing space via a first gas passage.

(2) Second processing space: A second processing space is provided which is isolated from the surrounding environment. A gas contained in the first processing space is introduced into the second processing space via a second gas passage.

(3) Oxygen concentration detection element: Adapted to measure the oxygen concentration of gas contained in the first processing space.

(4) Fist oxygen pumping element: Formed of an oxygen-ion conductive solid electrolyte. Electrodes are formed on opposing surfaces of the oxygen pumping element. The first oxygen pumping element pumps out oxygen from the first processing space or pumps oxygen into the first processing space so as to adjust the oxygen concentration of the measurement gas introduced into the first processing space and measured by the oxygen concentration detection element. In this manner, the oxygen concentration falls within a range such that water vapor contained in the measurement gas is not substantially decomposed, that is, within a range which does not substantially initiate a reaction of decomposing water vapor contained in the measurement gas.

(5) Oxidation catalyst element: Adapted to accelerate combustion of a combustible gas component contained in the gas which has been introduced into the second processing space from the first processing space via the second gas passage.

(6) Combustible gas component concentration information generation/output section: Adapted to have an output which varies according to the amount of oxygen consumed by reaction of the combustible gas component contained in the gas introduced into the second processing space, to thereby provide information regarding the concentration of the combustible gas component of the measurement gas.

The present invention also provides a gas sensor system having the following characteristic features.

(A) Gas sensor: Configured to have the following constituent features.

(1) First processing space: A first processing space is provided which is isolated from the surrounding environment. A measurement gas is introduced into the first processing space via a first gas passage.

(2) Second processing space: A second processing space is provided which is isolated from the surrounding environment. A gas contained in the first processing space is introduced into the second processing space via a second gas passage.

(3) Oxygen concentration detection element: Adapted to measure the oxygen concentration of gas contained in the first processing space.

(4) First oxygen pumping element: Formed of an oxygen-ion conductive solid electrolyte. Electrodes are formed on opposing surfaces of the oxygen pumping element. The first oxygen pumping element pumps out oxygen from the first processing space or pumps oxygen into the first processing space.

(5) Oxidation catalyst element: Adapted to accelerate combustion of a combustible gas component contained in a gas having an oxygen concentration which has been adjusted by the first oxygen pumping element and then introduced into the second processing space from the first processing space via a second gas passage.

(6) Combustible gas component concentration information generation/output section: Adapted to have an output which varies according to the amount of oxygen consumed by reaction of the combustible gas component contained in the gas introduced into the second processing space, to thereby provide information regarding the concentration of the combustible gas component of the measurement gas.

(B) First oxygen pumping operation control means: Adapted to control the first oxygen pumping element so as to adjust the oxygen concentration of the measurement gas introduced into the first processing space and measured by the oxygen concentration detection element within a range such that water vapor contained in the measurement gas is not substantially decomposed.

The gas sensor and the gas sensor system of the present invention can measure a combustible gas component selected singly or in combination from the group consisting of, for example, hydrocarbon (HC), carbon monoxide and hydrogen.

In the configuration described above, the oxygen concentration of a measurement gas (e.g., the exhaust gas of an internal combustion engine) as measured by the oxygen concentration detection element is adjusted to a predetermined value by operation of the first oxygen pumping element. The thus-treated gas is introduced into the second processing space, where a combustible gas component undergoes combustion through the aid of the oxidation catalyst. The combustible gas component concentration information generation/output section has a signal output which varies depending on the amount of oxygen consumed by combustion of the combustible gas component, to thereby provide information regarding the concentration of the combustible gas component of the measurement gas. The most important feature of the gas sensor and the gas sensor system of the present invention resides in that by operation of the first oxygen pumping element, the oxygen concentration of the measurement gas introduced into the first processing space is adjusted within a range such that water vapor contained in the measurement gas is not substantially decomposed. That is, by substantially suppressing hydrogen generation due to decomposition of water vapor caused by the oxygen concentration adjustment, a reduction in measurement accuracy in measuring a combustible gas component concentration can be prevented which would otherwise result from combustion of the generated hydrogen. Also, the gas sensor and the gas sensor system of the present invention exhibit excellent selectivity toward HC, particularly methane, and thus can measure methane concentration more accurately than do conventional gas sensors.

When a measurement gas contains carbon dioxide and the carbon dioxide is decomposed, carbon monoxide, which is a combustible gas component, is generated as in the case of water vapor from which hydrogen is generated. Combustion of the thus-generated carbon monoxide may reduce the accuracy in detecting the combustible gas component. In such a case, the first oxygen pumping element is further preferably configured so as to adjust the oxygen concentration of the measurement gas introduced into the first processing space and measured by the oxygen concentration detection sensor within a range that carbon dioxide is not substantially decomposed. Since the oxygen concentration at which decomposition of carbon dioxide occurs is generally lower than the oxygen concentration at which decomposition of water vapor occurs, the decomposition of carbon dioxide is concurrently prevented by employing an oxygen concentration condition that prevents the decomposition of water vapor.

Another gas sensor of the present invention has the same structure as that of the above-described gas sensor except that the first oxygen pumping element has the following structure:

(4') First oxygen pumping element: Formed of an oxygen-ion conductive solid electrolyte. Electrodes are formed on opposing surfaces of the oxygen pumping element. The first oxygen pumping element pumps out oxygen from the first processing space or pumps oxygen into the first processing space so as to adjust the oxygen concentration of the measurement gas introduced into the first processing space and measured by the oxygen concentration detection element within a range of $10^{-12}$ atm to $10^{-6}$ atm.

Another gas sensor system of the present invention has the same structure as that of the above-described gas sensor system, except that the first oxygen pumping operation control means has the following structure:

(B)' First oxygen pumping operation control means: Adapted to control the first oxygen pumping element so as to adjust the oxygen concentration of the measurement gas introduced into the first processing space and measured by the oxygen concentration detection element within the range of $10^{-12}$ atm to $10^{-6}$ atm.

In the above-described configuration, the oxygen concentration of the first processing space achieved by operation of the first oxygen pumping element is adjusted within the above range, thereby suppressing decomposition of water vapor and thus improving the sensing accuracy of the gas sensor or the gas sensor system. Because the oxygen concentration achieved by such adjustment is far higher than an oxygen concentration of $10^{-20}$ atm to $10^{-14}$ atm as conventionally required, the first oxygen pumping element has a smaller burden even when measuring, for example, under lean-burn conditions. Thus, the service life of the oxygen pumping element is enhanced. Also, the power required to operate the oxygen pumping element is not very high, and a control circuit and other peripheral devices can be provided at low cost. Also, in this case, the first oxygen pumping element (or the oxygen pumping control means) is preferably configured such that the oxygen concentration of a measurement gas introduced into the first processing space and measured by the oxygen concentration detection element is adjusted such that the oxygen concentration falls within a range such that water vapor contained in the measurement gas is not substantially decomposed.

When the oxygen concentration of a measurement gas introduced into the first processing space becomes less than $10^{-12}$ atm, decomposition of water vapor, if contained therein, becomes conspicuous. As a result, hydrogen generated by decomposition of water vapor may significantly impair accuracy in measuring a combustible gas component concentration. By contrast, when the oxygen concentration of the first processing space is in excess of $10^{-6}$ atm, combustion of a combustible gas component becomes conspicuous in the first processing space. Accordingly, the combustible gas component concentration of a gas introduced into the second processing space becomes small with a potential failure to attain a predetermined measurement accuracy. More preferably, the oxygen concentration of the first processing space is adjusted to a value of $10^{-11}$ atm to $10^{-9}$ atm.

For example, when the gas sensor is set at a working temperature of 600° C. to 800° C. and the water vapor concentration of a measurement gas varies within a range of about 5% to 15%, oxygen that maintains equilibrium with water vapor and hydrogen has a minimum partial pressure of about $10^{-12}$ atm. When the partial pressure of oxygen drops below the minimum value, decomposition of water vapor progresses, thereby affecting accuracy in measuring a combustible gas component concentration. Therefore, in this case, the oxygen concentration of the first processing space is preferably set to a value greater than the above minimum partial pressure of oxygen.

As used herein, unless specifically described otherwise, the oxygen concentration within the first processing space means the oxygen concentration measured by the oxygen concentration detection element. For example, when a part of a combustible gas component contained in a measurement gas burns and consumes oxygen, the oxygen concentration detected by the oxygen concentration detection element is not necessarily equal to the oxygen concentration before the consumption of oxygen as a result of combustion. Also, the oxygen concentration may vary at locations within the first processing space due to the presence of a porous electrode disposed to face the first processing space which catalyzes combustion of a combustible gas component, or due to oxygen pumping of the oxygen pumping element. In this case as well, the oxygen concentration as measured by the oxygen concentration detection element is considered to represent the oxygen concentration within the first processing space. When the oxygen concentration of a measurement gas introduced into the first processing space is relatively high, the first oxygen pump operates to mainly pump oxygen out from the first processing space in order to cause the oxygen concentration as measured by the oxygen concentration detection element to fall within the range of $10^{-12}$–$10^{-6}$ atm. By contrast, the first oxygen pump operates to pump oxygen into the first processing space when an increased amount of a combustible gas component (e.g., carbon monoxide, hydrogen, ammonia) burns while the first electrode, described below, is used as a catalyst for combustion, and oxygen consumption due to the combustion proceeds.

DESCRIPTION OF SYMBOLS

Figure 1:
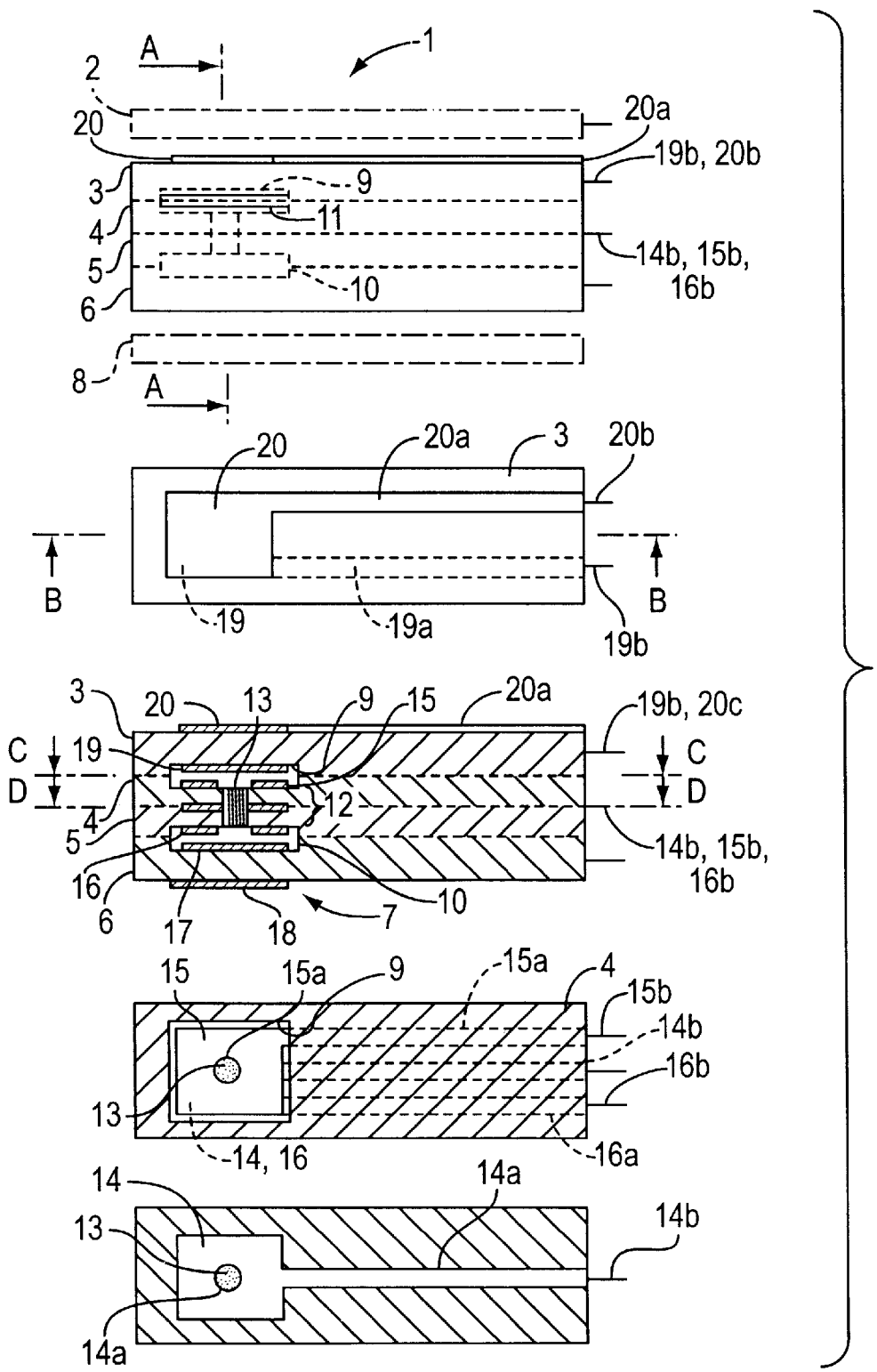
FIG. 1 is a front view showing an embodiment of a gas sensor of the present invention, a plane view, a sectional view taken along line B—B, a sectional view taken along line C—C, and a sectional view taken along line D—D.

1: exhaust gas sensor
2: first heater
3: first oxygen pumping element
4: first oxygen concentration cell element (oxygen concentration detection element)
5: second oxygen concentration cell element (combustible gas component concentration information generation/output section)
6: shield member
7: second oxygen pumping element (combustible gas component concentration information generation/output section)
8: second heater
9: first processing space
10: second processing space
11: first gas passage
12: partition wall
13: second gas passage
14: oxygen reference electrode
15: first electrode
16: third electrode (oxidation catalyst section)
17: fifth electrode (oxidation catalyst section)
19: seventh electrode
50: gas sensor system 50
51: peripheral circuit
52: microprocessor
53: CPU
54: ROM
54*a*: work area
54*b*: calculated value storage area
55: RAM
55*a*: control program
55*b*: concentration conversion table
56: I/O port
57: differential amplifier (first oxygen pumping operation control means)
70: differential amplifier (second oxygen pumping operation control means)
111: pumping cell unit
111*a*: fitting projections (pump-cell-side fitting portions)
112: sensor cell unit
112*a*: fitting depression (sensor-cell-side fitting portions)
151: main electrode layer
152: surface electrode layer

DETAILED DESCRIPTION OF THE PREFERRED EMBODIMENTS

In the gas sensor and the gas sensor system of the present invention, in order to more effectively prevent or suppress the decomposition of water vapor, the first oxygen pumping element is preferably operated to adjust the oxygen concentration within the first processing space to a level such that part of the combustible gas component contained in the introduced measurement gas burns while the first electrode is used as an oxidation catalyst. Furthermore, in another preferred embodiment of the invention, when detection selectivity toward hydrocarbon (especially, methane or the like having a relatively low combustion activity) is to be improved, the oxygen concentration within the first processing space as measured by the oxygen concentration detection element is preferably adjusted within a range such that a component (e.g., carbon monoxide, hydrogen, ammonia) having a higher combustion activity than the hydrocarbon to be detected is burned more readily than the hydrocarbon. This adjustment improves the detection selectivity toward hydrocarbon (e.g., methane). The oxygen concentration range varies depending on the combustion catalytic activity of the first and seventh electrodes, described below, toward various combustible gas components. However, the oxygen concentration range generally is $10^{-12}$–$10^{-6}$ atm, preferably $10^{-11}$–$10^{-9}$ atm.

In the gas sensor (and the gas sensor system) described above, at least either the first gas passage for introducing a measurement gas into the first processing space from outside or the second gas passage for establishing communication between the first processing space and the second processing space may be configured so as to serve as a diffusion-controlling passage for permitting gas flow at a constant diffusion resistance. This feature suppresses the compositional variation of a gas introduced into the first or second processing space to a small degree for a constant period of time as determined by the diffusion resistance of the passage even under conditions where the gas concentration of an atmosphere subjected to measurement varies. Thus, accuracy in measuring a combustible gas composition concentration can be improved. Specifically, the diffusion-controlling passage may assume the form of small holes or slits or may comprise formed of any of various throttling mechanisms or porous metals or ceramics having communicating pores formed therein.

In the gas sensor and the gas sensor system described above, the oxygen concentration detection element may comprise a first oxygen concentration cell element. The first oxygen concentration cell element is formed of an oxygen-ion conductive solid electrolyte having first and second electrodes formed on opposing surfaces thereof. One of the electrodes (first electrode) is disposed so as to be exposed to (adjacent to) the first processing space. Furthermore, the combustible gas component concentration information generation/output section comprises a second oxygen concentration cell element formed of an oxygen-ion conductive solid electrolyte having third and fourth electrodes formed on opposing surfaces thereof. One of the electrodes (third electrode) is disposed so as to be exposed to (adjacent to) the second processing space. The second oxygen concentration cell element is adapted to detect the oxygen concentration of the gas within the second processing space. The first and third electrodes may each assume the form of a porous electrode having oxygen molecule desorption capability. The third electrode can be adapted to serve as the oxidation catalyst having an oxidation-related catalytic activity toward a combustible gas component contained in the measurement gas. The first electrode has a lower oxidation-related catalytic activity than the third electrode. Furthermore, in yet another preferred embodiment, the combustible gas component concentration information generation/output section generates the combustible gas component concentration detection information on the basis of the concentration cell electromotive force developed by the second oxygen concentration cell element.

In the above configuration, the oxygen concentration within the second processing space is measured by means of the second oxygen concentration cell element. Since the concentration cell electromotive force of the second oxygen concentration cell element changes depending on the amount of oxygen consumed by combustion of the combustible gas component, the combustible gas component concentration information generation/output section can easily generate the combustible gas component concentration detection information based on the concentration cell electromotive force. Furthermore, the first electrode has an oxidation-related catalytic activity that is lower than that of the third electrode. Thus, at least a portion of a residual combustible gas component which has not been burned in the first processing space can be reliably burned in the second processing space, thereby improving sensor sensitivity. Also, since the electrode (third electrode) of the second concentration cell element exposed to the second processing space also serves as an oxidation catalyst section, the structure of the gas sensor or the gas sensor system is further simplified.

In the gas sensor of the present invention, a more preferable result is obtained by employing an electrode having the following structure. Specifically, a first oxygen pumping element comprises an oxygen-ion conductive solid electrolyte having seventh and eighth electrodes formed on opposing surfaces thereof, and the seventh electrode is disposed so as to be exposed to the first processing space. When the component to be detected is CO or HC, the seventh electrode is composed of two layers, namely, a porous main electrode layer and a porous surface electrode layer. The porous main electrode layer is made of a Pt—Au alloy (Au content: 1 wt. % or less) or Pt. The porous surface electrode layer covers the main electrode layer to thereby form a surface layer portion of the seventh electrode. The surface electrode layer is made of a material selected from the group consisting of a metal containing Au or Ag as a main component, a Pt—Au alloy, an Au—Pd alloy, a Pt—Ag alloy and a Pt—Ni alloy (hereinafter collectively referred to as an "inactive metal"). The seventh electrode has an oxidation-related catalytic activity toward the combustible gas component that is lower than that of the third electrode or lower than that of the third and fifth electrodes. As used herein, the term "X-Y alloy" means an alloy in which a metal component having the highest content by weight is X, and a metal component having the second highest content by weight is Y. The alloy may be an X-Y binary system alloy or a higher-order system alloy containing X, Y and other alloy components.

Materials for the electrodes of the oxygen concentration cell element or the oxygen pumping element must have a sufficient catalytic activity for desorption and recombination of oxygen molecules. Pt single metal, for example, is an excellent material in this point. However, if this material is used for the electrode exposed to the first processing space, the material has an extremely high combustion catalytic activity toward a combustion gas component. Therefore, the catalytic activity must be decreased slightly. For example, as conventionally practiced, Au, whose combustion catalytic activity is low, is mixed with Pt in an amount of up to about 20 wt. %, thereby forming a Pt—Au alloy. However, when the Au content increases, a considerable decrease in activity for desorbing oxygen molecules occurs concurrently with a decrease in the combustion catalytic activity toward a combustible gas component. Therefore, these two catalytic activities are difficult to balance.

This problem can be solved by employing the above-described multilayer electrode, in which the surface of the porous main electrode layer formed of a Pt—Au alloy or Pt having a high activity for desorbing oxygen molecules is covered with the porous surface electrode layer formed of an inactive metal having a low combustion catalytic activity toward a combustible gas component. This structure allows for a convenient adjustment to decrease the combustion catalytic activity toward a combustible gas component to the extent possible, while maintaining a sufficient level of oxygen molecule desorption activity.

In the present invention, the surface electrode layer is preferably formed of an Au-containing porous metal that has a considerably low combustion catalytic activity toward CO or HC and some degree of catalytic activity for desorption and recombination of oxygen molecules. Alternatively, a porous metal containing Ag as a main component, a porous Pt—Au alloy (Au content: 5 wt. % or more), a porous Pt—Pb alloy (Pb content: 1 wt. % or more), a porous Pt—Ag alloy (Ag content: 1 wt. % or more), a porous Pt—Ni alloy (Ni content: 1 wt. % or more), and the like may be used.

The surface electrode layer and the main electrode layer may be arranged such that these layers are in indirect contact with each other via one or more other layers. However, the use of a two-layer structure comprising the main electrode layer and the surface electrode layer simplifies the manufacturing process. In this case, when the surface electrode layer is formed of an Au-containing porous metal that contains Au as a main component, the remarkable effect of suppressing the combustion catalytic activity toward a combustible gas component can be obtained, while a sufficient level of oxygen molecule desorption activity is also maintained.

The above-described multilayer electrode is advantageously employed as the seventh electrode of the oxygen pump which does not require a sharp response to oxygen concentration. The above-described multilayer electrode can be used as the first electrode of the oxygen concentration cell element. However, in order to further improve accuracy in measuring the oxygen concentration within the first processing space using the oxygen concentration cell element, the first electrode is preferably formed of Pt, a Pt—Au alloy, or a Pt—Ag alloy. In this case, because combustion of a combustible gas component that is caused by the first electrode within the first processing space can be suppressed by making the area of the first electrode smaller than that of the seventh electrode, the loss caused by the combustion of the combustible gas component within the first processing space can be decreased, so that the sensor sensitivity can be further increased.

When a Pt—Au alloy or a Pt—Ag alloy is used as the first electrode, Au or Ag is added to suppress the combustion catalytic activity toward CO or HC. In this case, when the Au or Ag content exceeds 1 wt. %, the oxygen molecule desorption activity decreases excessively, resulting in deterioration of the oxygen concentration detection performance. By contrast, when the Au or Ag content is less than 1 wt. %, almost no effect of suppressing the combustion catalytic activity is expected. Au and Ag may be added together to Pt such that their total content does not exceed 1 wt. %.

When detection selectivity for hydrocarbon among various combustible gas components must be improved, components having a higher combustion activity than do hydrocarbon are preferably burned more readily than the hydrocarbon to be detected. In this case, as described above, the oxygen concentration within the first processing space as measured by the oxygen concentration detection element is adjusted. Furthermore, the combustion catalytic activity of first electrode or the seventh electrode exposed to the first processing space and the temperature within the first processing space are important factors in improving the measurement selectivity. When the seventh electrode is formed of the above-described multilayer electrode having a relatively low combustion catalytic activity and the first electrode is formed of Pt or a Pt alloy having a high combustion catalytic activity, a hydrocarbon component (e.g., methane) having a slightly low combustion activity does not burn much, while components such as carbon monoxide, hydrogen and ammonia which have a higher combustion activity readily burn on the first electrode. As a result, an environment convenient for selective measurement of hydrocarbon components is created. When the temperature within the first processing space increases, the combustion reaction proceeds easily, and the difference in combustion catalytic activity between electrodes made of different materials is not so apparent. This is disadvantageous for the selective measurement of hydrocarbon components. However, when the seventh electrode has the above-described multilayer structure, a considerably large difference in catalytic activity between the seventh electrode and the first electrode formed of Pt or the like is produced even at considerably high temperatures (e.g. 700–800° C.), so that selective measurement of hydrocarbon components can be performed effectively.

When the seventh electrode is formed into the above-described multilayer structure, the gas sensor of the present invention can be manufactured in accordance with the method comprising the following steps.

(1) A substrate electrode layer forming step which comprises forming a substrate electrode pattern containing an unfired main electrode layer of material powder for the main electrode layer of the seventh electrode on an unfired solid electrolyte compact of the oxygen-ion conductive solid electrolyte layer constituting said first oxygen pumping element, and integrally firing the unfired main electrode layer with the unfired solid electrolyte compact to form on the oxygen-ion conductive solid electrolyte layer a substrate electrode layer containing the main electrode layer; and (2) a surface electrode layer forming step which comprises forming a layer of material powder for the surface electrode layer on the substrate electrode layer, and subjecting to secondary firing at a temperature lower than the integrally firing temperature to thereby form the surface electrode layer. The layer of material power may be formed, for example, by applying a of paste of the material powder onto the main electrode layer.

Because the substrate electrode layer containing the main electrode layer is formed of a high-melting point metal such as Pt or a Pt—Au or Pt—Ag alloy having the above-described composition, the substrate electrode layer can be fired concurrently with a solid electrolyte ceramic, such as zirconia, that constitutes the main portion of each element. However, when the surface electrode layer is formed of an Au-containing metal, which has a low melting point, maintaining the porous state of the substrate electrode layer becomes difficult when it is fired together with a solid electrolyte ceramic. In addition, Au diffuses into the substrate electrode layer, and therefore it becomes difficult to achieve the effect of suppressing the combustion catalytic activity. In order to solve this problem, the above-described process can be employed in which the surface electrode layer is subjected to secondary firing at a temperature lower than that used for integrally firing the substrate electrode layer and the solid electrolyte layer. This is to bond the surface electrode layer to the substrate electrode layer by baking. Thus, a multilayer electrode having a desired performance is obtained.

The components (e.g., Au) of the surface electrode layer may diffuse into the main electrode layer during the secondary firing or when the sensor is used at high temperature. For example, even if the main electrode layer is substantially formed of Pt, Au may diffuse from the surface electrode layer into the main electrode layer so that Au constituting the main electrode layer is converted into a Pt—Au alloy. If the diffusion of the material of the surface electrode layer into the main electrode layer proceeds excessively, the thickness of the surface electrode layer becomes insufficient, or in an extreme case, the surface electrode layer disappears. For example, when the surface electrode layer is desirably formed mainly of Au and the main electrode layer is desirably formed mainly of Pt, the temperature for secondary firing is preferably set to about 800–1050° C. in order to prevent excessive diffusion of Au into the main electrode layer. When the secondary firing temperature is less than 800° C., firing of the surface electrode layer becomes insufficient with the possibility of delamination of the surface electrode layer occurring due to insufficiently close contact. By contrast, when the secondary firing temperature is greater than 1050° C., the thickness of the surface electrode layer becomes insufficient due to diffusion of the Au component, or firing proceeds excessively, so that the porous structure is lost. In this case, the oxygen permeability that the porous electrode must have becomes difficult to maintain. When Au is mixed in the constituent metal of the main electrode layer in an amount of about 3–10 wt. % (for example, 10 wt. %) from the beginning, the diffusion of Au from the surface electrode layer into the main electrode layer can be suppressed because the extent of solid solution formation of Au into Pt is relatively small (about 5 wt. %) at 800° C. Thus, the drawbacks such as a reduction in thickness of the surface electrode layer can be effectively avoided.

The manufacturing method comprising the above-described secondary firing step can be performed efficiently in a preferred embodiment, when the gas sensor of the present invention is constructed such that a pumping cell unit including the first oxygen pumping element is formed separately from a sensor cell unit including the oxygen concentration detection element, the second processing space and the combustible gas component concentration information generation/output section; and the pumping cell unit and the sensor cell unit are joined and integrated with each other via a bonding material. In this case, the pumping cell unit is manufactured by firing such that the substrate electrode layer is formed without formation of the surface electrode layer; the secondary firing is performed in order to form the surface electrode layer on the substrate electrode layer of the pumping cell unit; and the pumping cell unit is integrated with the sensor cell unit, which has been separately manufactured by firing. Thus, the gas sensor is obtained. Preferably, a pump-cell-side fitting portion is formed in the pumping cell unit, and a sensor-cell-side fitting portion for engaging the pump-cell-side fitting portion is formed in the sensor cell unit. In this case, positioning during joining can be easily performed by engaging the pump-cell-side fitting portion and the sensor-cell-side fitting portion. Thus, the manufacturing efficiency of the sensor can be improved.

The first and second oxygen concentration cell elements may be formed of an oxygen-ion conductive solid electrolyte composed mainly of $ZrO_2$ ($ZrO_2$ solid electrolyte). In the oxygen concentration cell element formed of a $ZrO_2$ solid electrolyte, one electrode is in contact with a gas to be measured, which gas contains oxygen and a combustible gas component, while the other electrode is in contact with a reference atmosphere having a constant oxygen concentration. The electromotive force of the oxygen concentration cell element varies abruptly when the gas composition falls outside a stoichiometric composition in which oxygen and a combustible gas component are present in a proper ratio so that they completely react with each other. When an ordinary gasoline engine or diesel engine is operated under lean-burn conditions, a measurement gas emitted from the engine contains combustible gas components in a total concentration of about 0 to 1000 ppmc (ppmc: parts per million carbon equivalent). A measurement gas having such a combustible gas component concentration is introduced into the first processing space, and the oxygen concentration of the introduced measurement gas is adjusted to $10^{-7}$ atm (preferably $10^{-9}$ atm) or lower, as described previously. As a result, a gas introduced into the second processing space from the first processing space has a stoichiometric composition or a composition shifted slightly toward a rich condition. Thus, the output from the second oxygen concentration cell element is increased, thereby improving the sensitivity of the gas sensor.

As described above, the concentration cell electromotive force of the second oxygen concentration cell element changes depending on the amount of oxygen consumed by combustion of the combustible gas component. Therefore, in another preferred embodiment, the concentration cell electromotive force output provides the combustible gas component concentration detection information. In this case, the second oxygen concentration cell element serves as the combustible gas component concentration information generation/output section. In some cases, the above-described concentration cell electromotive force does not change linearly with the concentration of the combustible gas component. In such a case, the gas sensor system may be provided with an output conversion section having the following structure. Specifically, the output conversion section includes electromotive force-concentration relation storage means, concentration determination means and concentration value output means. The electromotive force-concentration relation storage means stores information regarding the relationship between the concentration cell electromotive force and the combustible gas component concentration. The concentration determination means determines a combustible gas component concentration corresponding to the concentration cell electromotive force output from the second oxygen concentration cell element, based on the relationship between the concentration cell electromotive force and the combustible gas component concentration stored in the storage means. The concentration value output means outputs the thus-determined concentration value. Thus, the sensor output can used directly.

The above-described gas sensor may be constructed as follows. That is, first and second oxygen concentration cell elements and a second oxygen pumping element are provided. The first and second oxygen concentration cell elements have the same structure as described above. The second oxygen pumping element is formed of an oxygen-ion conductive solid electrolyte having electrodes formed on opposing surfaces thereof. One of the electrodes (the fifth electrode) is disposed such that it is exposed to the second processing space. The second oxygen pumping element pumps oxygen into the second processing space from the outside. The second oxygen pumping element pumps oxygen into the second processing space in order to compensate for a reduction of oxygen due to combustion of the combustible gas component to thereby maintain the oxygen concentration within the second processing space substantially constant. At that time, the second oxygen pumping element outputs a pumping current or a pumping voltage as the combustible gas component concentration detection information. In this way, the second oxygen pumping element serves as the combustible gas component concentration information generation/output section.

The gas sensor system corresponding to the above-described measurement gas sensor may be constructed as follows. That is, first and second oxygen concentration cell elements, a second oxygen pumping element and a second oxygen pumping operation control means are provided. The first and second oxygen concentration cell elements have the same structure as described above. The second oxygen pumping element is formed of an oxygen-ion conductive solid electrolyte having electrodes formed on opposing surfaces thereof. One of the electrodes (the fifth electrode) is disposed such that it is exposed to the second processing space. The second oxygen pumping element pumps oxygen into the second processing space from the outside. The second oxygen pumping operation control means controls the second oxygen pumping element so as to pump oxygen into the second processing space to thereby compensate for a reduction of oxygen due to combustion of the combustible gas component. As a result, the oxygen concentration within the second processing space is maintained substantially constant. The second oxygen pumping element pumps oxygen into the second processing space in order to compensate for a reduction of oxygen due to combustion of the combustible gas component to thereby maintain the oxygen concentration within the second processing space substantially constant. At that time, the second oxygen pumping element outputs a pumping current or a pumping voltage as the combustible gas component concentration detection information. In this way, the second oxygen pumping element serves as the combustible gas component concentration information generation/output section.

When the above-described structure is employed, the pumping current or pumping voltage of the second oxygen pumping element varies linearly with respect to the combustible gas component concentration. Therefore, a sensor output that is easily utilized can be obtained even when the above-described output conversion section is not provided. Since one electrode (the fifth electrode) of the second oxygen pump is newly disposed such that it is exposed to the second processing space, the following structure can be used. Specifically, in another preferred embodiment the first, third and fifth electrodes each assumes the form of a porous electrode having oxygen molecule desorbent capability. At least one of the third and fifth electrodes serves as an oxidation catalyst having an oxidation-related catalytic activity toward a combustible gas component contained in the measurement gas. Furthermore, the oxidation-related catalytic activities of the first, third, and fifth electrodes are adjusted such that the amount of oxygen consumed by combustion of the combustible gas component in the second processing space becomes greater than that consumed in the first processing space. In the second oxygen pumping element, only one of the third and fifth electrodes may be formed to have a higher oxidation-related catalytic activity than that of the first electrode. Alternatively, both the third and fifth electrodes may be formed to have a higher oxidation-related catalytic activity than that of the first electrode. In this case as well, the first, third and fifth electrodes may be formed of metals selected from the above-described high-activity metal group and low-activity metal group such that their oxidation-related catalytic activities satisfy the above-described relationship.

In another preferred embodiment of the gas sensor and gas sensor system of the present invention, the first processing space and the second processing space may be arranged such that a partition wall formed of an oxygen-ion conductive solid electrolyte is disposed therebetween. In this case, the second gas passage is formed in the partition wall so as to establish communication between the first processing space and the second processing space, and an oxygen reference electrode is embedded into the partition wall at a thicknesswise intermediate portion. The first electrode is formed on the partition wall so as to be exposed to the first processing space. The first electrode, the oxygen reference electrode and a portion of the partition wall interposed between the first electrode and the oxygen reference electrode constitute the first oxygen concentration cell element. Also, the third electrode is formed on the partition wall so as to be exposed to the second processing space. The third electrode, the oxygen reference electrode and a portion of the partition wall interposed between the third electrode and the oxygen reference electrode constitute the second oxygen concentration cell element. Furthermore, the first oxygen pumping element is arranged opposite the partition wall with the first processing space disposed therebetween. This arrangement enables the two oxygen concentration cell elements to share the oxygen reference electrode, thereby implementing a compact sensor. When the second oxygen pumping element is provided, the second oxygen pump in another preferred embodiment is arranged opposite the partition wall with the second processing space disposed therebetween.

As described above, and in reference to FIG. 10, the first oxygen concentration cell element is defined as comprising an oxygen-ion conductive solid electrolyte having first (15) and second (14) electrodes formed on opposing surfaces thereof. The second oxygen concentration cell element is defined as comprising an oxygen-ion conductive solid electrolyte having third (16) and fourth (14) electrodes formed on opposing surfaces thereof. The first oxygen pumping element is defined as comprising an oxygen-ion conductive solid electrolyte having seventh (19) and eighth (20) electrodes formed on opposing surfaces thereof. The second oxygen pumping element is defined as comprising an oxygen-ion conductive solid electrolyte having fifth (17) and sixth (18) electrodes formed on opposing surfaces thereof. Electrode 15 is exposed to the first processing space, whereas electrodes 16 and 17 are exposed to the second processing space. Furthermore, some of these electrodes may have a dual function. For example, in reference to FIG. 10, electrode 14 which is an oxygen reference electrode serves as both the second and fourth electrodes.

Various embodiments of the present invention will now be described with reference to the drawings and Examples, however, the present invention should not be construed as being limited thereto.

First Embodiment:

FIG. 1 shows a gas sensor 1 according to an embodiment of the present invention. The gas sensor 1 includes a first heater 2, a first oxygen pumping element (hereinafter referred to as the "first pumping element") 3, a first oxygen concentration cell element (hereinafter referred to as the "first cell element") 4, a second oxygen concentration cell element (hereinafter referred to as the "second cell element") 5, a shield member 6, and a second heater 8. These elements of the gas sensor 1 are in the shape of an elongated sheet and arranged in layers in this order so as to be integrated into a single unit. In the present embodiment, a second oxygen pump, described below, is not provided. A first processing space 9 is formed between the first pumping element 3 and the first cell element 4. A second processing space 10 is formed between the second cell element 5 and the shield member 6.

The elements 3 to 5 and the shield member 6 are formed of a solid electrolyte having oxygen-ion conductivity. A typical example of such a solid electrolyte is a $ZrO_2$ solid solution containing $Y_2O_3$ or CaO. Another example is a solid solution of $ZrO_2$ and an oxide of an alkaline earth metal or of a rare earth metal. $ZrO_2$ serving as a base material may include $HfO_2$. The present embodiment employs a solid electrolyte ceramic of $ZrO_2$ obtained through solid solution of $Y_2O_3$ or CaO. The first and second heaters 2 and 8, respectively, are known ceramic heaters and are adapted to heat the elements 3 to 5 to a predetermined working temperature (650° C. to 700° C.). An insulating layer (not shown in FIG. 1; an insulating layer 260 is shown in FIG. 4) is interposed between the elements 3 to 5 and the shield member 6. The insulating layer is primarily formed of $Al_2O_3$. The laminated sensor structure is formed by laminating and subsequent firing of ceramic green sheets (ceramic moldings), which become the elements and members 3 to 6.

Figure 2:
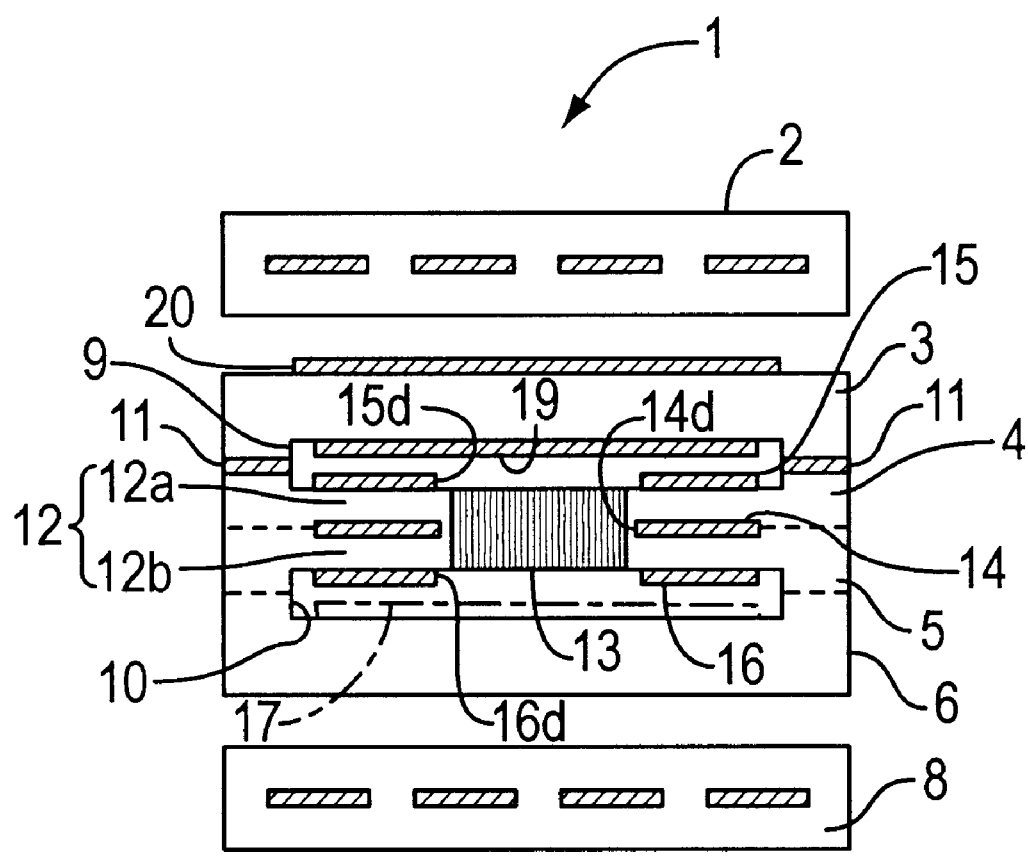
FIG. 2 is a sectional view taken along line A—A of FIG. 1.

First gas passages 11 are formed at both side wall portions of the first processing space 9 so as to establish communication between the first processing space 9 and an external atmosphere to be measured. Located on both widthwise sides of the first processing space 9 as shown in FIG. 2, the first gas passages 11 are interposed between and extend along the first pumping element 3 and the first cell element 4 in a longitudinal direction of the elements 3 and 4. The first gas passage 11 is formed of a porous ceramic body having communicating pores, which ceramic body is a porous fired body of $Al_2O_3$ or the like. Thus, the first gas passages 11 serve as diffusion-controlling passages for introducing a measurement gas into the first processing space 9 from the outside while a constant diffusion resistance is maintained.

The first cell element 4 and the second cell element 5 are arranged in adjacent layers. A partition wall 12, formed of an oxygen-ion conductive solid electrolyte, is interposed between the first processing space 9 and the second processing space 10. In other words, the first and second processing spaces 9 and 10, respectively, are arranged with the partition wall 12 interposed therebetween. A second gas passage 13 is formed in the partition wall 12 so as to establish communication between the first processing space 9 and the second processing space 10. An oxygen reference electrode 14 is embedded in the partition wall 12 at a thicknesswise intermediate portion. As in the case of the first gas passages 11, the second gas passage 13 is formed of a porous ceramic body and serves as a diffusion-controlling passage for introducing a gas into the second processing space 10 from the first processing space 9 while maintaining a constant diffusion resistance. The first and second gas passages 11 and 13, respectively, may assume the form of small holes or slits instead of being formed of a porous ceramic body (or a porous metallic body).

As shown in FIG. 2, a first electrode 15 is formed on the partition wall 12 so as to be exposed to the first processing space 9. A main portion of the first cell element 4 includes the first electrode 15, the oxygen reference electrode 14, and a portion 12a of the partition wall 12 interposed between the electrodes 15 and 14. A third electrode 16 is formed on the partition wall 12 so as to be exposed to the second processing space 10. A main portion of the second cell element 5 includes the third electrode 16, the oxygen reference electrode 14, and a portion 12b of the partition wall 12 interposed between the electrodes 16 and 14. Also, the first pumping element 3 has electrodes 19 and 20 formed on both surfaces thereof.

The electrodes 14 to 16, 19 and 20 have a reversible catalytic function (oxygen desorption related catalytic function), which catalyzes a desorption reaction for desorbing oxygen molecules therefrom in order to introduce oxygen into the solid electrolytes of the elements 3 to 5, and a recombination reaction for recombining with oxygen in order to make the solid electrolytes release oxygen. Materials for the electrode 19 of the first pumping element 3 and the first electrode 15 of the first cell element 4, which electrodes 19 and 15 are exposed to the first processing space 9, and that for the third electrode 16 of the second cell element 5, which electrode 16 is exposed to the second processing space 10, are selected such that the electrodes 19 and 15 have lower oxidation-catalytic activity (i.e., combustion) of a component to be measured, such as methane, than does the electrode 16. In the present embodiment, the electrodes 19 and 15 are formed of a Pt—Au alloy (for example, an alloy of Pt and 1% by weight of Au), and other electrodes are formed of Pt. These porous electrodes are formed in the following manner. In order to improve adhesion between an electrode and a substrate formed of a solid electrolyte ceramic, a metal or alloy powder serving as an electrode material is mixed with an appropriate amount of solid electrolyte ceramic powder similar to that used as the material for the substrate. The resulting mixture is formed into a paste. By using the paste, an electrode pattern is printed on a ceramic green sheet serving as a substrate, followed by firing. The electrodes 19 and 15 having lower oxidation-related catalytic activity may be formed of Au or a like metal which has an oxidation-related catalytic activity that is lower than that of a Pt—Au alloy. However, because a Pt—Au alloy and a solid electrolyte ceramic of $ZrO_2$ can be concurrently fired, the manufacturing efficiency of the gas sensor 1 is improved.

Figure 3A:
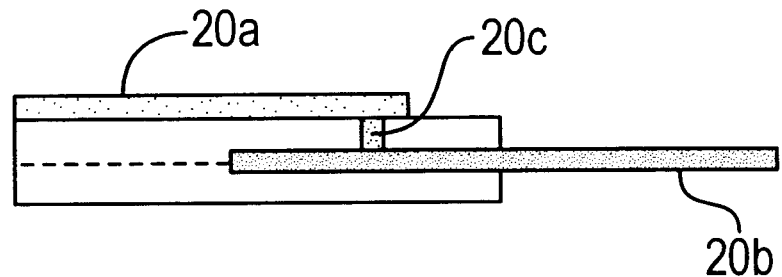
FIG. 3(a) is a sectional view showing an example of a connection between an electrode lead and a terminal.

As shown in FIG. 1, electrode leads 14a to 16a, 19a and 20a are integrally formed with the electrodes 14 to 16, 19 and 20, respectively, of the elements 3 to 5, and extend along a longitudinal direction of the elements 3 to 5 toward a sensor end portion. At the sensor end portion, the ends of connection terminals 14b to 16b, 19b and 20b are embedded in the elements 3 to 5. As illustrated in FIG. 3(a), which representatively shows the electrode lead 20a, each connection terminal (20b) is electrically connected to an end portion of each electrode lead (20a) by means of a conductor (20c). The conductor (20c) is formed in the element thickness direction by sintering a metallic paste. Furthermore, as shown in FIG. 2, through-holes 14d–16d are respectively formed in the electrodes 14–16 at a position corresponding to the second gas passage 13.

Figure 4A:
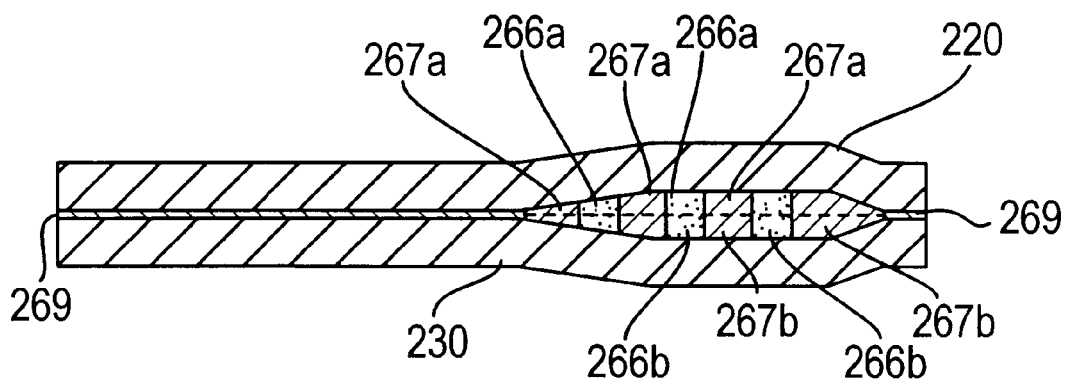
FIGS. 4(a) and (b) are explanatory views illustrating a process of forming a processing space in the gas sensor of FIG. 1.
Figure 4B:
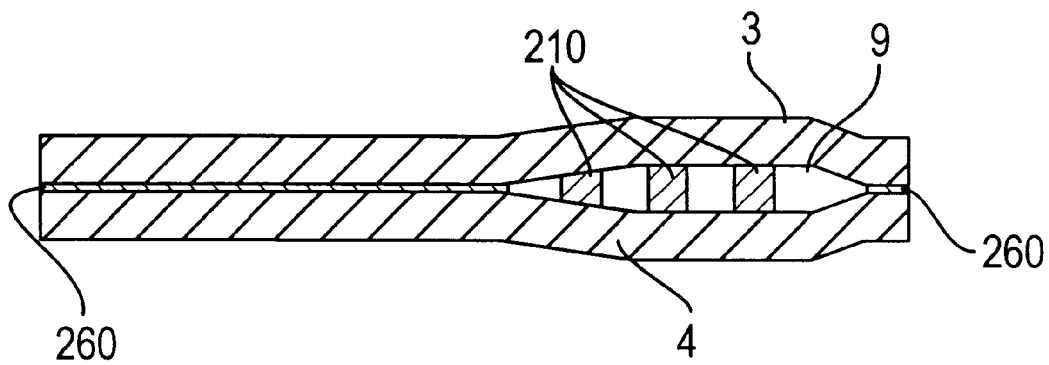

As shown in FIG. 4(b), in the first processing space 9 and the second processing space 10, supports 210 are formed in a scattered or staggered manner to thereby prevent the collapse of the spaces 9 and 10 during firing. The process of forming such a space structure will be described, taking the first processing space 9 as an example. As shown in FIG. 4(a), using a ceramic powder paste (for example, a paste of porous $Al_2O_3$ powder), support patterns 266a are formed on a ceramic green sheet 220 in a region for defining the first processing space 9. The ceramic green sheet 220 will be formed into the first pumping element 3. Likewise, support patterns 266b are formed on a ceramic green sheet 230 in a region for defining the first processing space 9. The ceramic green sheet 230 will be formed into the first cell element 4. The support patterns 266a and 266b will be formed into supports 210. By using a paste material (for example, carbon paste) which will be burned or decomposed during firing, auxiliary support patterns 267a are formed on a ceramic green sheet 220 in a region for defining the first processing space 9 so as not to overlap the support patterns 266a. Likewise, auxiliary support patterns 267b are formed on a ceramic green sheet 230 in a region for defining the first processing space 9 so as not to overlap the support patterns 266b. Furthermore, by using an $Al_2O_3$ powder paste, an insulating layer pattern serving as a bonding coat 269 is formed between the ceramic green sheets 220 and 230 in a region other than the region for defining the first processing space 9. The thickness of the insulating layer pattern is made smaller than that of the supports 210. Although not shown in FIG. 4, by using a paste of porous $Al_2O_3$ powder, communicating-portion patterns are formed on both sides of the region for defining the first processing space 9. Once fired, the communicating-portion patterns will become the first gas passages 11.

The thus-prepared assembly of the ceramic green sheets 220 and 230 is subjected to firing. As a result, as shown in FIG. 4(b), the support patterns 266a and 266b are united into the supports 210 between the first pumping element 3 and the first cell element 4, whereas the auxiliary patterns 267a and 267b disappear. The first processing space 9 is formed, while its size is maintained by the supports 210. As shown in FIG. 2, porous ceramic bodies form the first gas passages 11 on both widthwise sides of the first processing space 9. The first cell element 4 and the first pumping element 3 are bonded together in a region other than the first processing space 9 by means of the bonding coat 269 serving as the insulating layer 260.

Figure 5A:
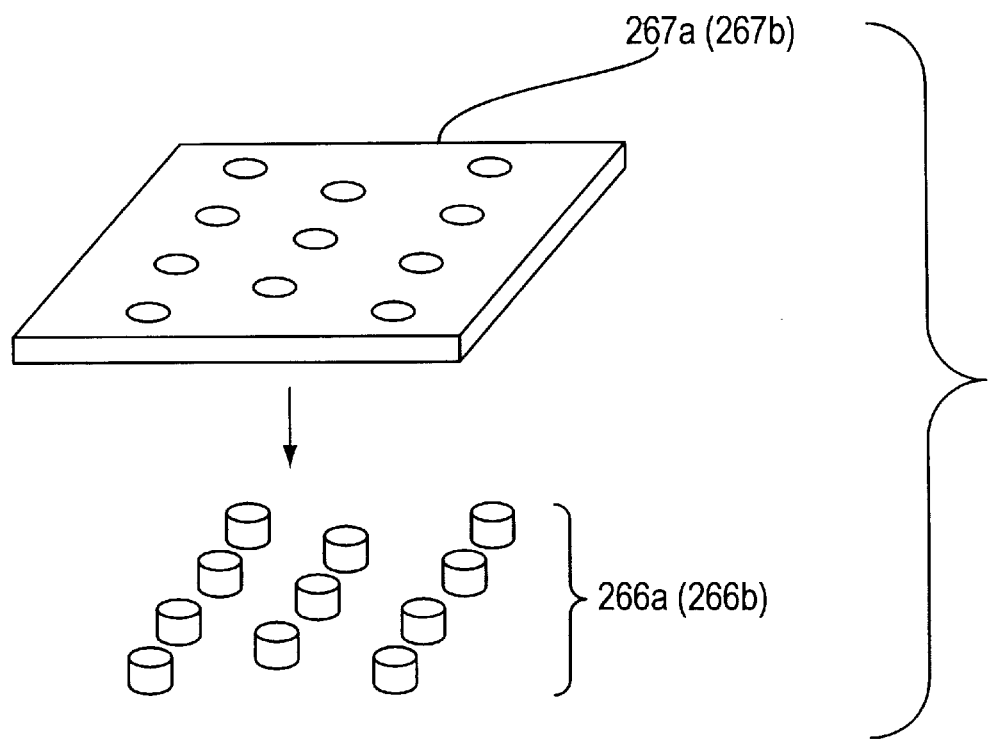
FIGS. 5(a) and (b) are explanatory views illustrating the process of forming the processing space in the gas sensor of FIG. 1.
Figure 5B:
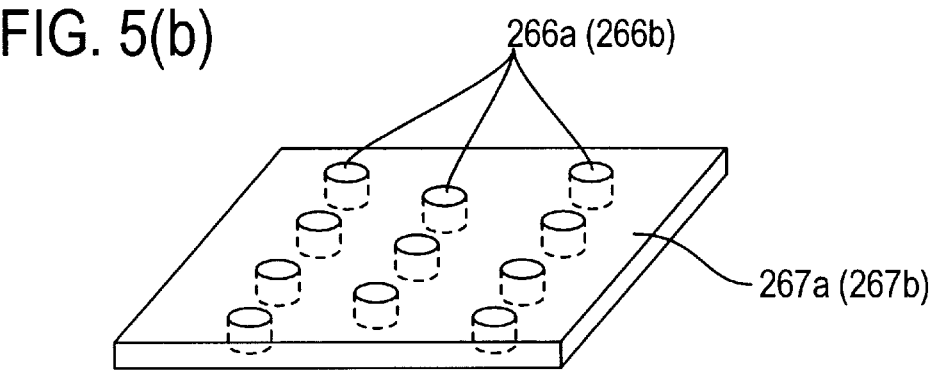

As shown in FIGS. 5(a) and 5(b), the support patterns 266a (266b) and the auxiliary support pattern 267a (267b) are complementarily formed to thereby form a substantial plane. When the green sheets 220 and 230 are superposed to each other as shown in FIG. 4(a), the reinforcing effect of the auxiliary support patterns 267a and 267b prevents or suppresses the collapse of the support patterns 266a and 266b butting against each other. As exaggeratedly shown in FIG. 4(a), even when the bonding coat 269 is made considerably thinner than the total thickness of the support patterns 266a and 266b, the green sheets 220 and 230 can be bonded together by means of the interposed bonding coat 269. Because the green sheets 220 and 230 are flexible, the bonding can be established through a slight flexure thereof. Thus, the green sheets 220 and 230 can be smoothly fired into a single unit.

Figure 3B:
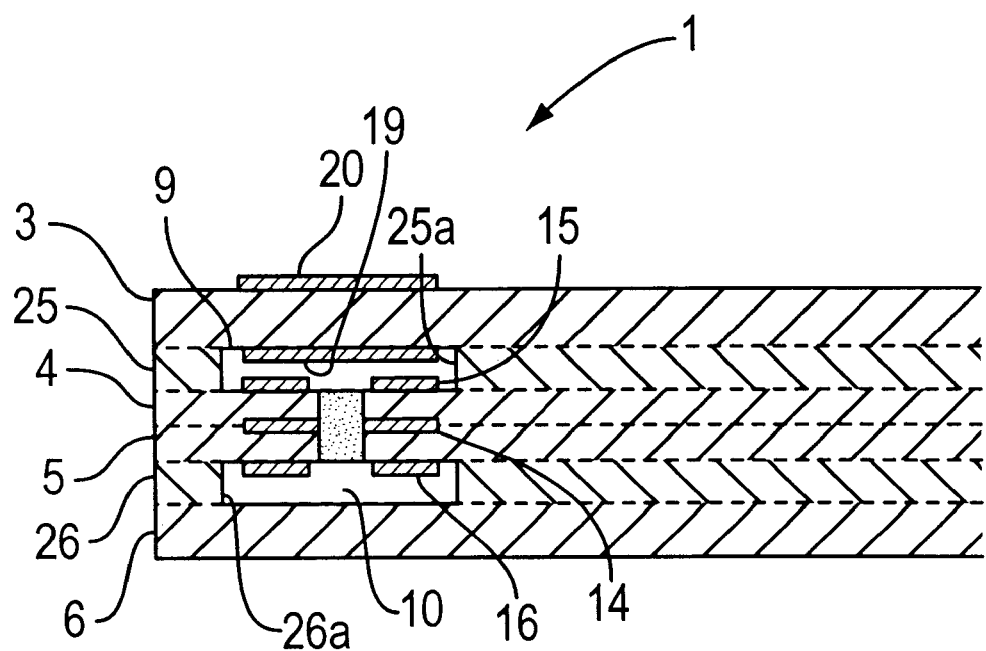
FIG. 3(b) is a sectional view showing a modification of the as sensor of FIG. 1.

As shown in FIG. 3(b), the first processing space 9 may be formed using a spacer 25 (that can be formed of a $ZrO_2$ solid electrolyte ceramic) having a space 25a for forming the processing space 9. In this case, the spacer 25 is sandwiched between the first pumping element 3 and the first cell element 4, which are then fired for integration. Similarly, the second processing space 10 may be formed using a spacer 26 which has a similar space 26a and which is interposed between the second cell element 5 and the shield member 6.

Next, an embodiment of a gas sensor system using the gas sensor 1 above is described as follows.

Figure 6:
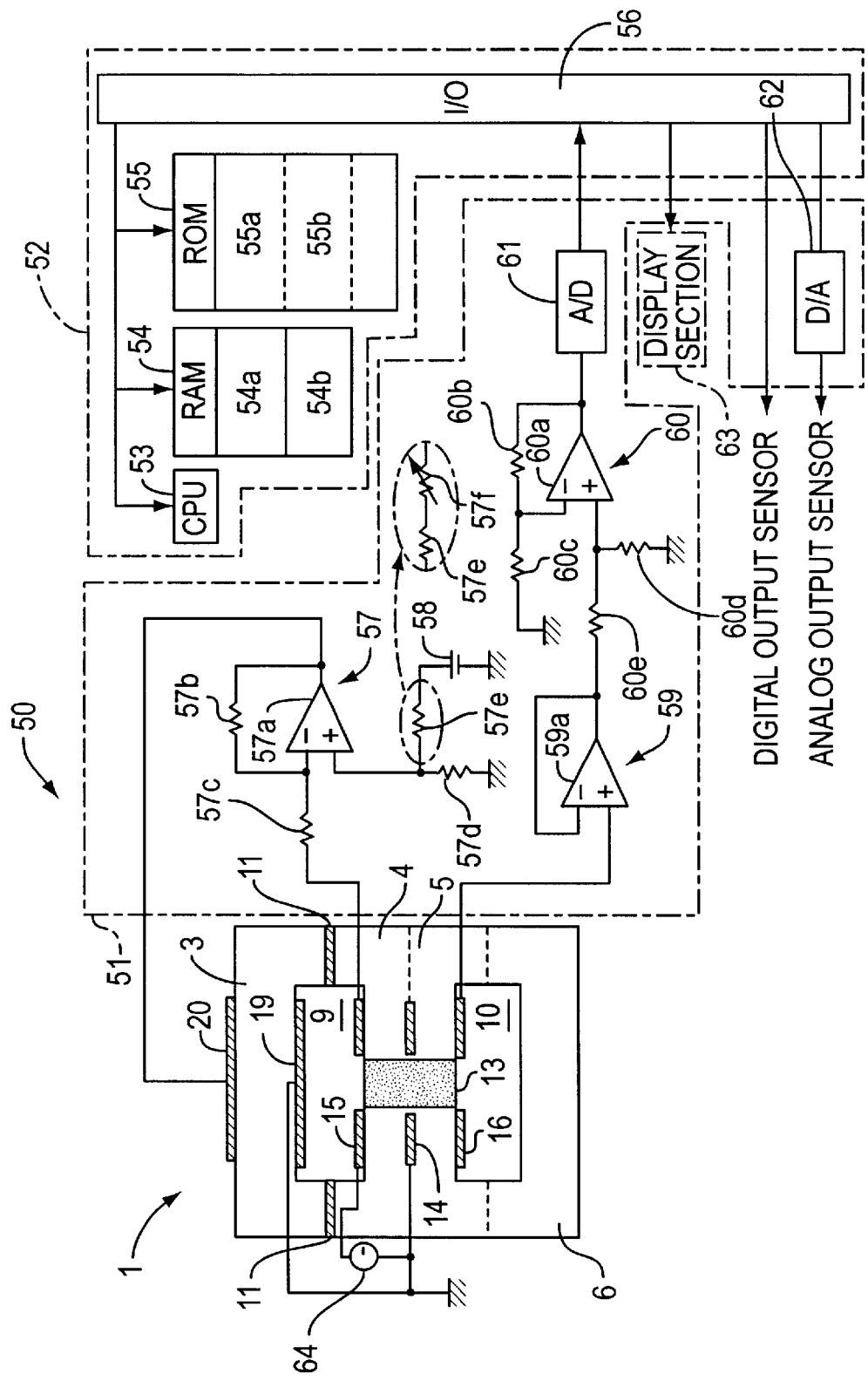
FIG. 6 is a block diagram showing a circuit configuration example of a gas sensor system 50 using the gas sensor of FIG. 1.

FIG. 6 shows an example of an electrical block diagram of a gas sensor system (hereinafter referred to as the "sensor system") using the gas sensor 1. Specifically, the gas sensor system 50 includes the gas sensor 1, a microprocessor 52, and a peripheral circuit 51 for connecting the gas sensor 1 to the microprocessor 52. The microprocessor 52 is a main portion of an output conversion unit and includes an I/O port 56 serving as an input/output interface, a CPU 53, a RAM 54, a ROM 55, etc. The CPU 53, the RAM 54, the ROM 55 and the like are connected to the I/O port 56. The RAM 54 has a work area 54a for the CPU 53, and a storage area 54b for storing calculated values of component concentration. The ROM 55 contains a control program 55a and an HC concentration conversion table 55b. The control program 55a is used for controlling the gas sensor system 50 in computing a component concentration and in outputting the computed component concentration. The CPU 53 serves as concentration determination means, and determines a component concentration according to the control program 55a stored in the ROM 55. The I/O port 56 serves as the concentration value output means.

In the gas sensor system 50, the gas sensor 1 operates in the following manner. The exhaust gas sensor 1 is heated to a predetermined working temperature by means of the first heater 2 and the second heater 8 shown in FIG. 2, etc. (either of the heaters may be omitted). The working temperature is a temperature at which the $ZrO_2$ solid electrolyte forming elements 3 to 5 is activated. While the gas sensor 1 is heated at its working temperature, a measurement gas is introduced into the first processing space 9 through the first gas passages 11. The first cell element 4 measures the oxygen concentration of the introduced measurement gas. Based on the oxygen concentration detected by the first cell element 4, the first pumping element 3 pumps out oxygen from or pumps oxygen into the gas contained in the first processing space 9 so as to bring the oxygen concentration to a predetermined target value of $10^{-12}$ atm to $10^{-6}$ atm (preferably $10^{-11}$ atm to $10^{-9}$ atm), in other words, to a predetermined target value at which water vapor contained in the measurement gas is not substantially decomposed. Generally, the oxygen concentration of the measurement gas is higher than the above target value. In this case, the first pumping element 3 operates so as to mainly reduce the oxygen concentration of the first processing space 9. When the oxygen concentration detected by the first cell element 4 falls within the range of $10^{-12}$ atm to $10^{-6}$ atm, the corresponding concentration cell electromotive force of the first cell element 4 falls within the range of about 300 mV (corresponding to $10^{-6}$ atm)–600 mV (corresponding to $10^{-12}$ atm)

After reducing the oxygen concentration to the above predetermined value, the gas contained in the first processing space 9 flows into the second processing space 10 through the second gas passage 13. Because the third electrode 16 has a higher oxidation-related activity than the first electrode 15 toward a combustible gas component such as HC or the like, a combustible gas component of the gas contained in the second processing space 10 is burned while the third electrode 16 serves as an oxidation catalyst. Thus, oxygen is consumed. The oxygen concentration of the second processing space 10 varies according to the oxygen consumption associated with the combustion, i.e., according to the concentration of a combustible gas component. Therefore, when the concentration is measured as the concentration cell electromotive force of the second cell element 5, the concentration of the combustible gas component contained in the measurement gas can be determined from the thus-measured concentration cell electromotive force.

On the surface of the shield member 6 disposed opposite to the partition wall 12 with the second processing space interposed therebetween, a porous metal layer 17 may be formed separately from the third electrode 16 so as to be exposed to the second processing space 10. The porous metal layer 17 may be formed of a metal, such as Pt, having a catalytic activity for the combustion of a combustible gas component which is higher than that of the electrodes 19 and 15. In this case, the porous metal layer 17, together with the third electrode 16, serves as an oxidation catalyst in order to increase the efficiency of combustion of a combustible gas component within the second processing chamber 10, thereby improving the sensitivity of the gas sensor 1. When the porous metal layer 17 has a sufficiently high catalytic activity, the third electrode 16 may be formed of a material having a low catalytic activity such as Pt—Au, as in the case of the electrodes 19 and 15.

The circuit configuration and operation of the gas sensor system 50 will be described in more detail with reference to FIG. 6, etc. In the gas sensor 1, the oxygen reference electrode 14 and the electrode 19 of the first pumping element 3 exposed to the first processing space 9 are grounded. The first electrode 15 of the first cell element 4 is connected to one input terminal of a differential amplifier 57. The differential amplifier 57 includes an operational amplifier 57a and peripheral resistors 57b to 57e. Thus, the concentration cell electromotive force E of the first cell element 4 is input to the differential amplifier 57. A power circuit 58 is connected to the other input terminal of the differential amplifier 57. The power circuit 58 outputs to the differential amplifier 57 a target electromotive force EC corresponding to a target oxygen concentration value. The differential amplifier 57 amplifies the difference between the electromotive force E of the first cell element 4 and the target electromotive force EC, and inputs the amplified difference to the electrode 20 of the first pumping element 3. Upon receiving the output from the differential amplifier 57, the first pumping element 3 pumps oxygen out from or into the first processing space 9 so that the electromotive force E (corresponding to the oxygen concentration of the first processing space 9) approaches the target electromotive force EC. That is, the differential amplifier 57 serves as the first oxygen pumping operation control means.

The power circuit 58 may be configured such that the target electromotive force EC is fixedly set by a fixed voltage source or such that the target electromotive force EC) can be variably set. For example, a variable resister 57f (or a pre-set variable resistor) may be interposed between the power circuit 58 and the operational amplifier 57a. In this case, the target electromotive force EC can be varied within a certain range by changing the electric resistance of the variable resistor 57f.

The concentration cell electromotive force of the second cell element 5 representing the oxygen concentration within the second processing space 10 is taken from the third electrode 16. Via a voltage follower circuit 59 including an operational amplifier 59a, the output from the third electrode 16 is input to an amplifying circuit 60. The amplifying circuit 60 includes an operational amplifier 60a and peripheral resistors 60b to 60e. The amplified signal is converted to a digital signal by an A/D converter 61 and is then input to the microprocessor 52. The first cell element 4 and the second cell element 5 share the common oxygen reference electrode 14. However, a constant-current regulated power source 64 causes a small DC current to continuously flow between the oxygen reference electrode 14 and the first electrode 15 (or the third electrode 16) in a direction such that oxygen is pumped into the oxygen reference electrode 14. This feature causes pores formed in the oxygen reference electrode 14 to be always filled with a reference gas of near 100% oxygen. Thus, an electromotive force of the first cell element 4 and of the second cell element 5 is increased, thereby improving the measuring accuracy and the measuring sensitivity of the gas sensor 1.

Figure 7:
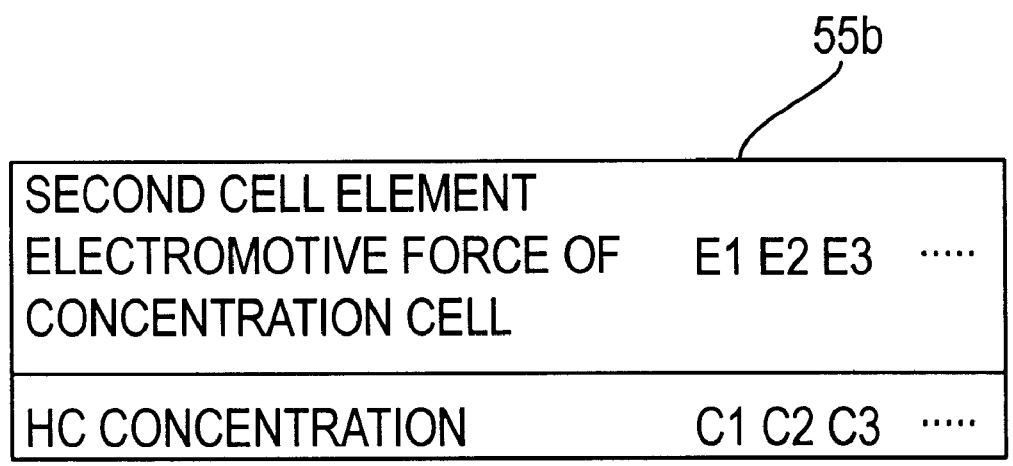
FIG. 7 is an explanatory diagram showing an example of the contents of a concentration conversion table.
Figure 8:
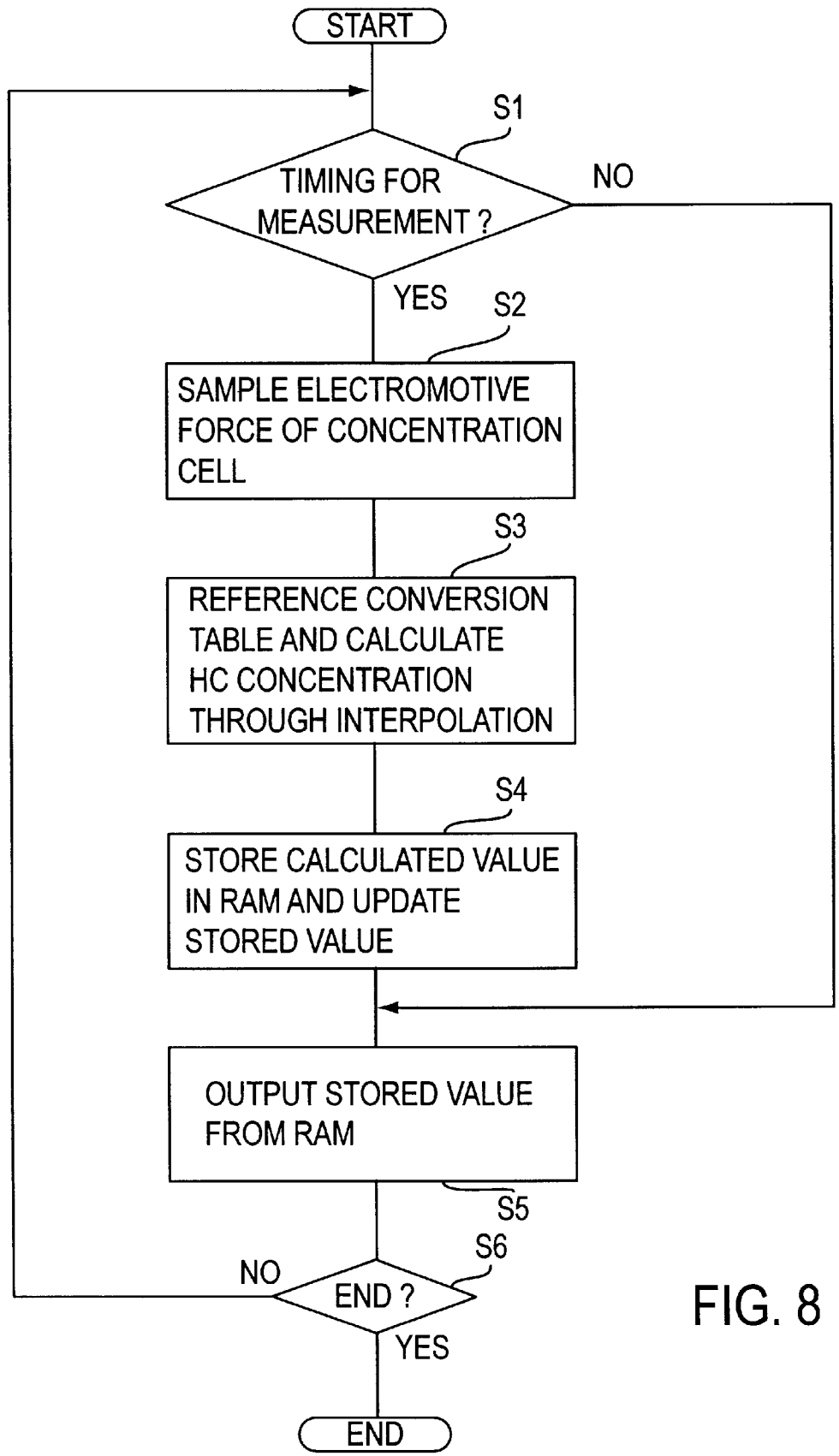
FIG. 8 is a flow chart showing a process flow of a control program of the gas sensor system 50 of FIG. 6.

The ROM 55 of the microprocessor 52 contains the control program 55a and the concentration conversion table 55b as described above. FIG. 7 shows an example the contents of the concentration conversion table 55b. The table 55b contains values of concentration cell electromotive force E1, E2, E3, etc. of the second cell element 5 corresponding to values of the combustible gas component concentration (for example, values of HC concentration) C1, C2, C3, etc. These values are previously determined based on experiments and the like. The CPU 53 (FIG. 6) performs a sensor output control as represented by the flowchart of FIG. 8 according to the control program 55a, using the RAM 54 as a work area.

Specifically, the measurement timing is metered using an unillustrated timer. In step S1, when the time for measurement is reached, processing proceeds to step S2. In step S2, the CPU 53 samples a concentration cell electromotive force output from the second cell element 5. In step S3, the CPU 53 calculates a combustible gas component concentration corresponding to the sampled value by interpolation while referencing the concentration conversion table 55b of FIG. 7. In step S4, the CPU 53 stores the calculated value into the calculated value storage area 54b of the RAM 54. The newly stored value overwrites a corresponding value previously stored in the area 54b. In step S5, the CPU 53 outputs the newly written calculated value from the I/O port 56 as information regarding the combustible gas component concentration of the measurement gas. The output may be either digital or analog. An analog output is obtained through digital-to-analog conversion effected by a D/A converter 62 connected to the I/O port 56. Furthermore, the concentration value may be displayed on a display section 63 connected to the I/O port 56.

In the thus-configured operational gas sensor system 50, the oxygen concentration of the measurement gas introduced into the first processing space 9 is reduced to a predetermined value of $10^{-12}$ atm to $10^{-6}$ atm by operation of the first pumping element 3. The thus-treated gas is introduced into the second processing space 10 and burned. The concentration cell electromotive force output of the second cell element 5 varies according to the oxygen consumption associated with the combustion. Thus, the concentration cell electromotive force output is utilized as information regarding the combustible gas component concentration of the measurement gas. By operation of the first pumping element 3, the oxygen concentration of the first processing space 9 is adjusted to a value such that water vapor contained in the measurement gas is not substantially decomposed. Even when the decomposition reaction is initiated, the degree of the reaction is very small. Thus, an impairment in accuracy in measuring a combustible gas component concentration is effectively prevented which would otherwise result from combustion of hydrogen generated from decomposition of water vapor.

Figure 9A:
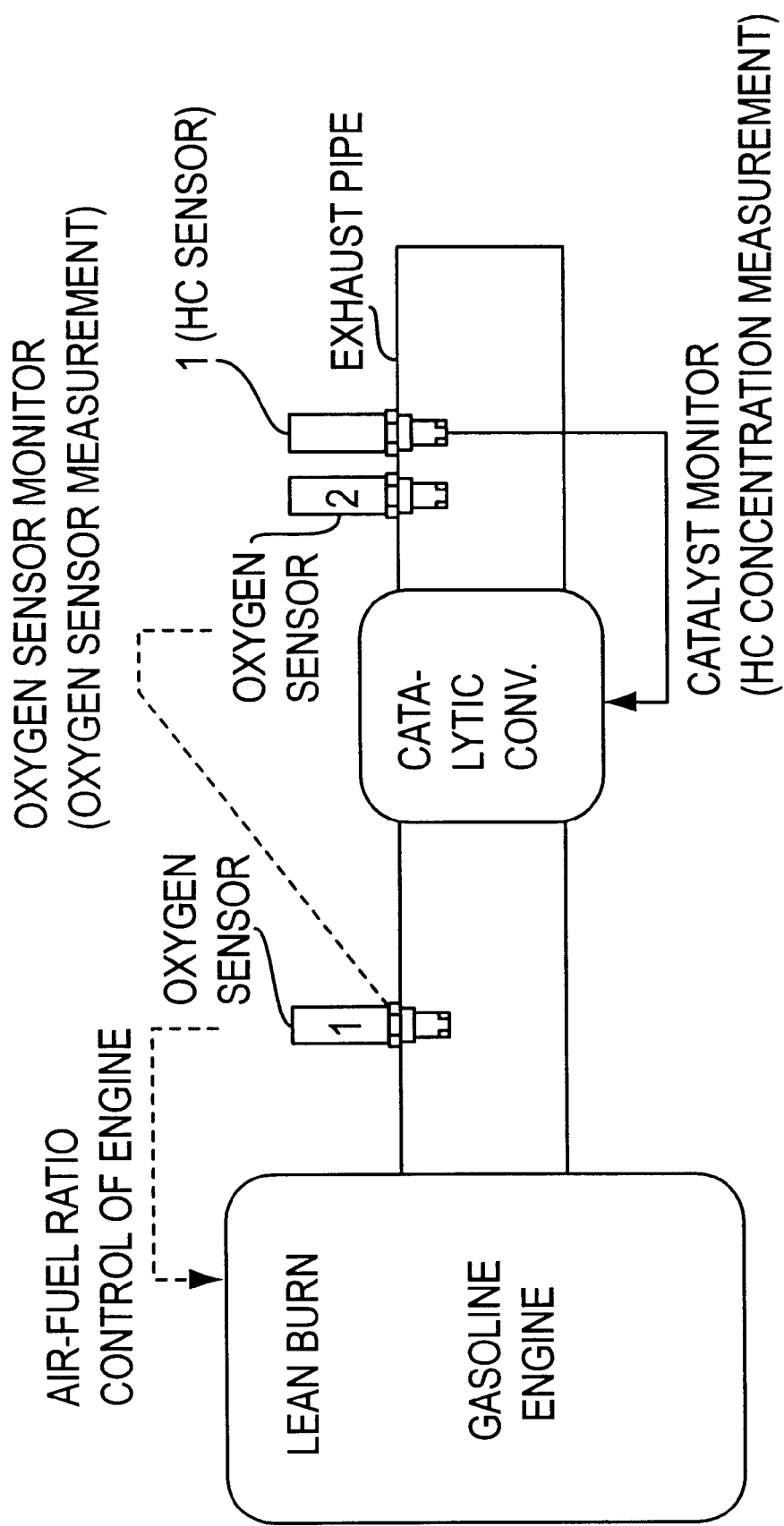
FIGS. 9(*a*) and 9(*b*) are schematic diagrams showing two applications of the gas sensor of the present invention.

Next, applications of the gas sensor 1 or the gas sensor system 50 will be described. FIG. 9(a) schematically shows an exhaust gas purification system of a gasoline engine. An oxygen sensor (1), a three way catalytic converter and an oxygen sensor (2) are attached onto an exhaust pipe in this order starting from the engine side. The gas sensor 1 of the present invention is provided on the downstream side of the oxygen sensor (2). The oxygen sensor (1) is used for air-fuel ratio control. The three way catalytic converter concurrently performs oxidation of HC and reduction of NOx to thereby purify an exhaust gas, which is a measurement gas. The exhaust gas sensor (2) measures the oxygen concentration of the purified exhaust gas. The gas sensor 1 measures the HC concentration of the purified exhaust gas, for example, in order to judge whether the catalyst is deteriorated.

The oxygen concentration of the exhaust gas may be measured using the separately provided oxygen sensor (2). However, because the current flowing through the first oxygen pumping element 3 of the gas sensor 1 changes linearly in accordance with the oxygen concentration of the exhaust gas, information regarding the oxygen concentration of the exhaust gas may be obtained from the current. In this case, the oxygen sensor (2) may be omitted.

Figure 9B:
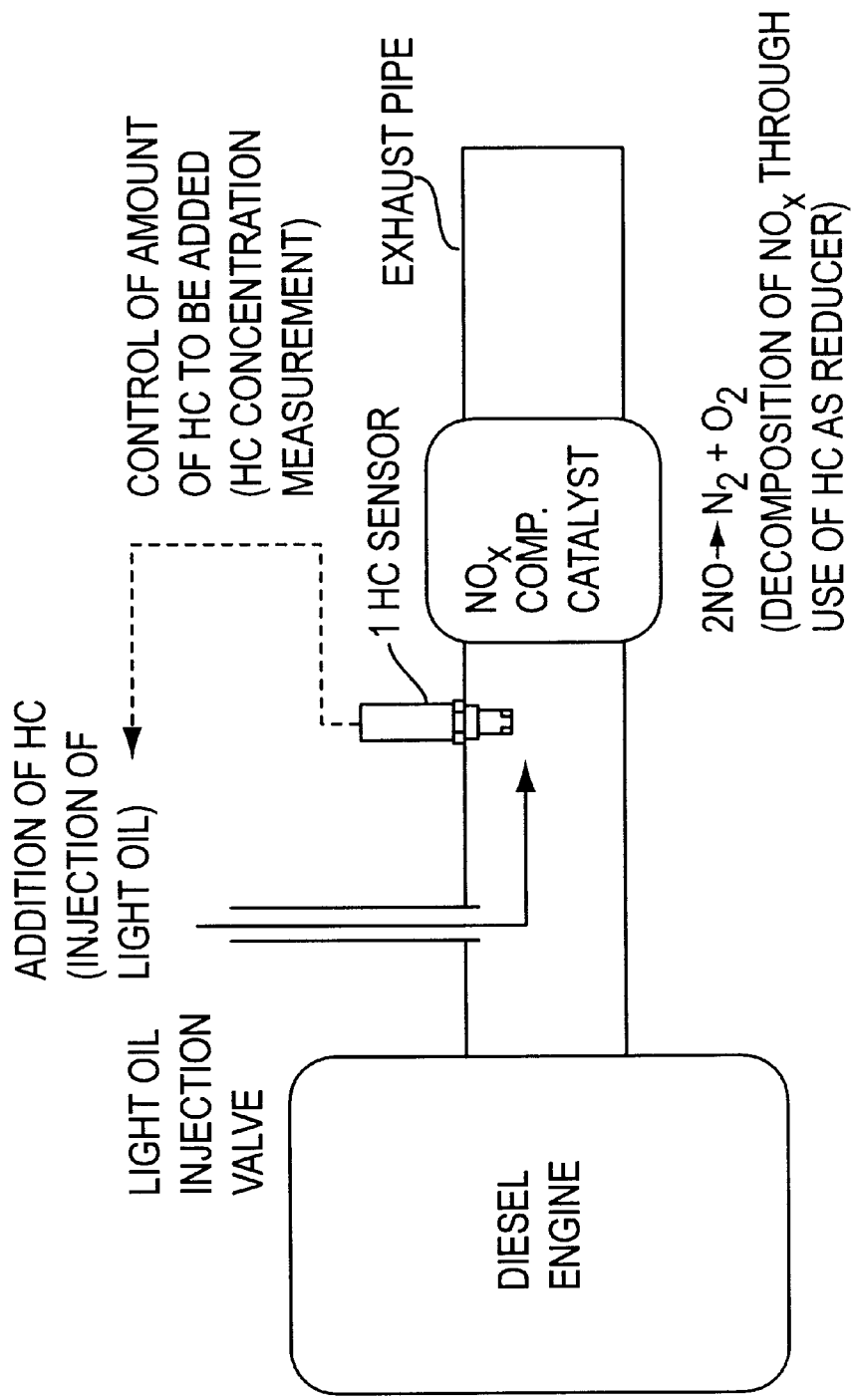

FIG. 9(b) schematically shows an exhaust gas purification system of a diesel engine. A light oil injection valve and an NOx decomposition catalyst are attached onto an exhaust pipe in this order starting from the engine side. The light oil injection valve is used for injecting light oil serving as an HC source into an exhaust gas. The NOx decomposition catalyst decomposes NOx into nitrogen and oxygen while using HC added through light oil injection as a reducer, thereby purifying the exhaust gas. The gas sensor 1 of the present invention is disposed on the upstream side of the NOx decomposition catalyst and monitors the HC concentration of the light-oil-injected exhaust gas in order to feedback-control the amount of light oil to be injected into the exhaust gas.

In the gas sensor 1, the first cell element 4 and the second cell element 5 are each formed of a $ZrO_2$ solid catalyst. In the case of an oxygen concentration cell element formed of a $ZrO_2$ solid electrolyte and configured such that one electrode is in contact with a gas to be measured, which gas contains oxygen and a combustible gas component, whereas the other electrode is in contact with a reference atmosphere having a constant oxygen concentration, its electromotive force varies abruptly when the gas composition falls outside a stoichiometric composition in which oxygen and a combustible gas component are present in a proper ratio so that they completely react with each other. When an ordinary gasoline engine or diesel engine is operated under lean-burn conditions, an exhaust gas is emitted from the engine contains combustible gas components in a total concentration of about 0 to 1000 ppmC. An exhaust gas having such a combustible gas component concentration is introduced into the first processing space 9, and the oxygen concentration of the introduced exhaust gas is adjusted to $10^{-7}$ atm (preferably $10^{-9}$ atm) or lower as described above. As a result, a gas introduced into the second processing space 10 from the first processing space 9 has a stoichiometric composition or a composition shifted slightly toward a rich condition. Thus, the output electromotive force of the second cell element 5 is increased, thereby improving the sensitivity of the gas sensor 1.

Figure 10:
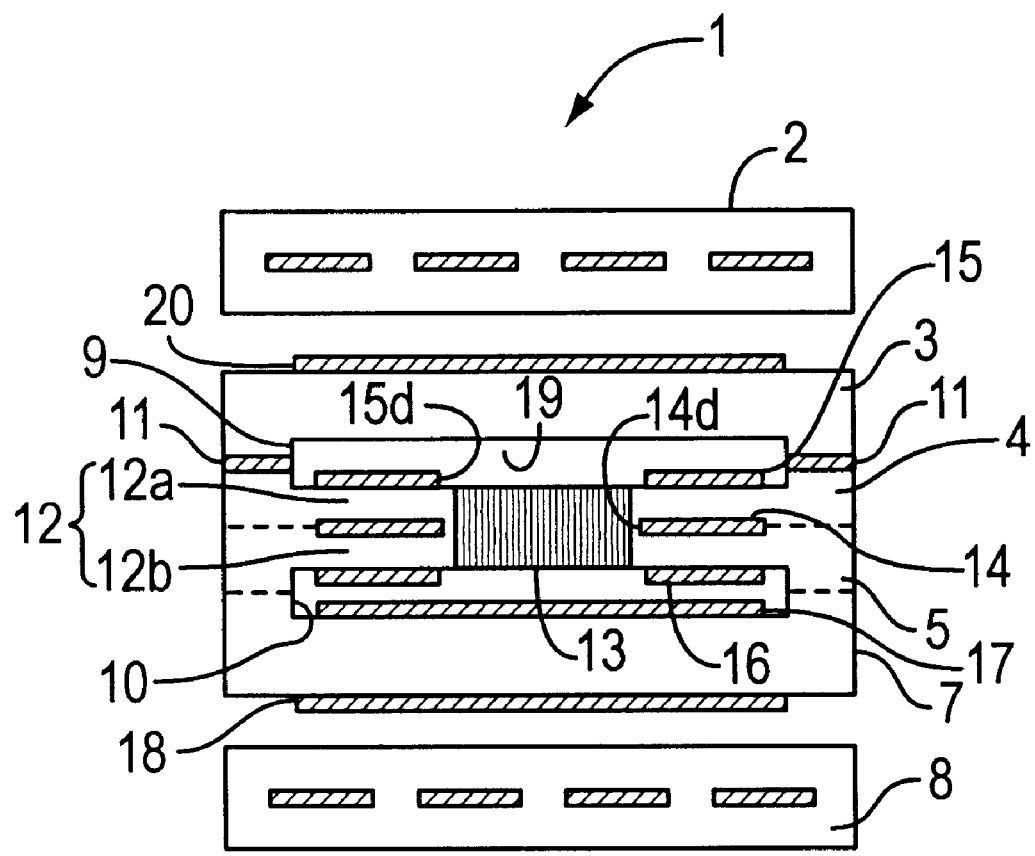
FIG. 10 is a sectional view showing another modification of the gas sensor of FIG. 1.

In the gas sensor 1, as shown in FIGS. 1 and 10, a second oxygen pumping element (hereinafter referred to as the "second pumping element") 7 may be provided in place of the seal member 6 on the side of the second processing space 10. The structure of the second pumping element 7 is substantially the same as that of the first pumping element 3. An electrode 17 is formed on the surface exposed to the second processing space 10, and an electrode 18 is formed on the opposite surface. The electrode exposed to the second processing space 10 is referred to as the "fifth electrode 17".

In this case, the first pumping element 3 and the first cell element 4 form a main portion of the first processing space forming section, and the second cell element 5 and the second pumping element 7 form a main portion of the second processing space forming section. The operation of this exhaust gas sensor 1 is as follows. Unlike the above-described exhaust gas sensor in which the concentration cell electromotive force of the second cell element 5 is output as the oxygen concentration within the second processing space 10, the second pumping element 7 pumps oxygen into the second processing space 10 to compensate for a reduction of oxygen due to the combustion of the combustible gas component, so that the oxygen concentration within the second processing space 10 is made substantially constant. A pumping current (or a pumping voltage) at that time is output as the combustible gas component concentration detection information.

Figure 11:
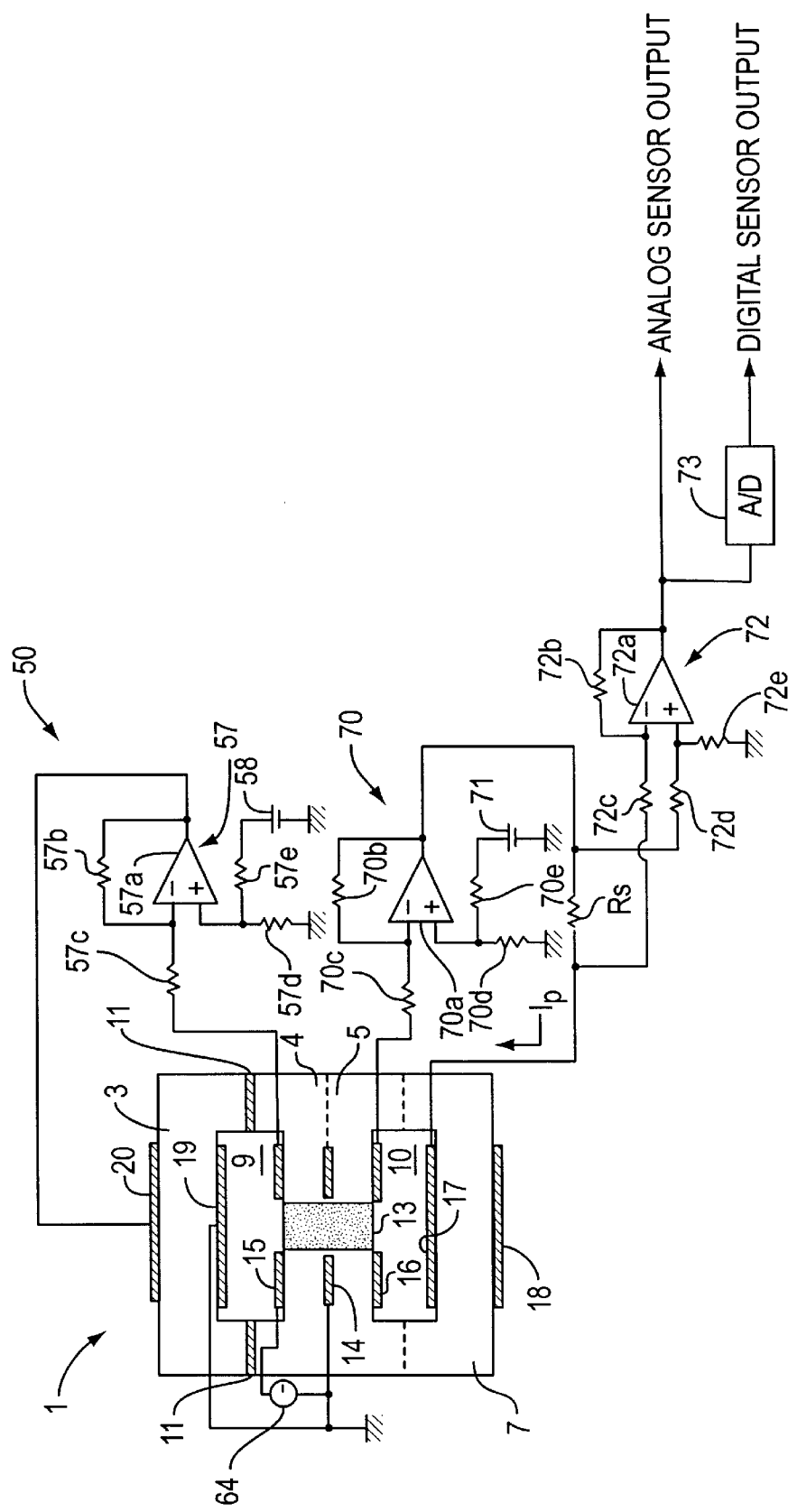
FIG. 11 is a block diagram showing a circuit configuration example of a gas sensor system 50 using the gas sensor of FIG. 10.

FIG. 11 shows the circuit diagram of the gas sensor system 50 in this case. The structure on the first processing space 9 side is completely the same as that shown in FIG. 6. The structure on the second processing space 10 side is modified as follows. The third electrode 16 of the second cell element 5 is connected to one input terminal of a differential amplifier 70. The differential amplifier 70 includes an operational amplifier 70a and peripheral resistors 70b to 70e. Thus, the concentration cell electromotive force E' of the second cell element 5 is input to the differential amplifier 70. A power circuit 71 is connected to the other input terminal of the differential amplifier 70. The power circuit 71 outputs to the differential amplifier 70 a target electromotive force EC' corresponding to a target oxygen concentration value.

The differential amplifier 70 amplifies the difference between the concentration cell electromotive force E' and the target electromotive force EC', and inputs the amplified difference to the electrode 17 of the second pumping element 7. Upon receiving of the output from the differential amplifier 70, the second pumping element 7 pumps oxygen out from or into the first processing space 10 so that the concentration cell electromotive force E' (corresponding to the oxygen concentration of the second processing space 10) of the second cell element 5 approaches the target electromotive force EC'. That is, the differential amplifier 70 serves as the second oxygen pumping operation control means. In order to suppress decomposition of water vapor contained in the gas introduced from the first processing space 9, the target electromotive force EC' for the second processing space 10 side is preferably set to be greater than that set for the first processing space 9 side. In this case, the second pumping element 7 operates to increase the oxygen concentration within the second processing space 10.

When the concentration cell electromotive force E of the second cell element 5 becomes substantially constant, the pumping current of the second pumping element 7 also becomes substantially constant. As the concentration of the combustible gas component contained in the gas introduced to the second processing space 10 increases, the amount of consumed oxygen increases, so that the amount of oxygen pumped into the second processing space 10 by the second pumping element 7, i.e., the pumping current of the second pumping element 7 increases. Specifically, the pumping current of the second pumping element 7 changes linearly with respect to an increase in concentration of the combustible gas component. Accordingly, without any correction or conversion, the pumping current can be used as a sensor output having a high linearity. For example, in FIG. 11, a resistor RS for current detection is interposed in the output line of the differential amplifier 70, and the voltage generated across the resistor RS is amplified by means of a differential amplifier 72 (composed of an operational amplifier 72a and peripheral resistors 72b–72e). The thus-amplified pump current is output in the form of a voltage signal. This voltage signal is used as an analog sensor output as such. Alternatively, after digital conversion using an A/D converter 73, the voltage signal can be used as a digital sensor output.

In the gas sensor 1 having the above-described structure, the fifth electrode 17 of the second pumping element 7 is newly disposed so as to be exposed to the second processing space 10. In such a structure, when the amount of oxygen consumed associated with combustion of the combustible gas component within the second processing space 10 must be greater than that in the first processing space 9, one of the third electrode 16 and the fifth electrode 17 is formed to have a higher oxidation-related catalytic activity than does the first electrode 15. Alternatively, both the third electrode 16 and the fifth electrode 17 may be formed to have a higher oxidation related catalytic activity than does the first electrode 15.

Figure 19:
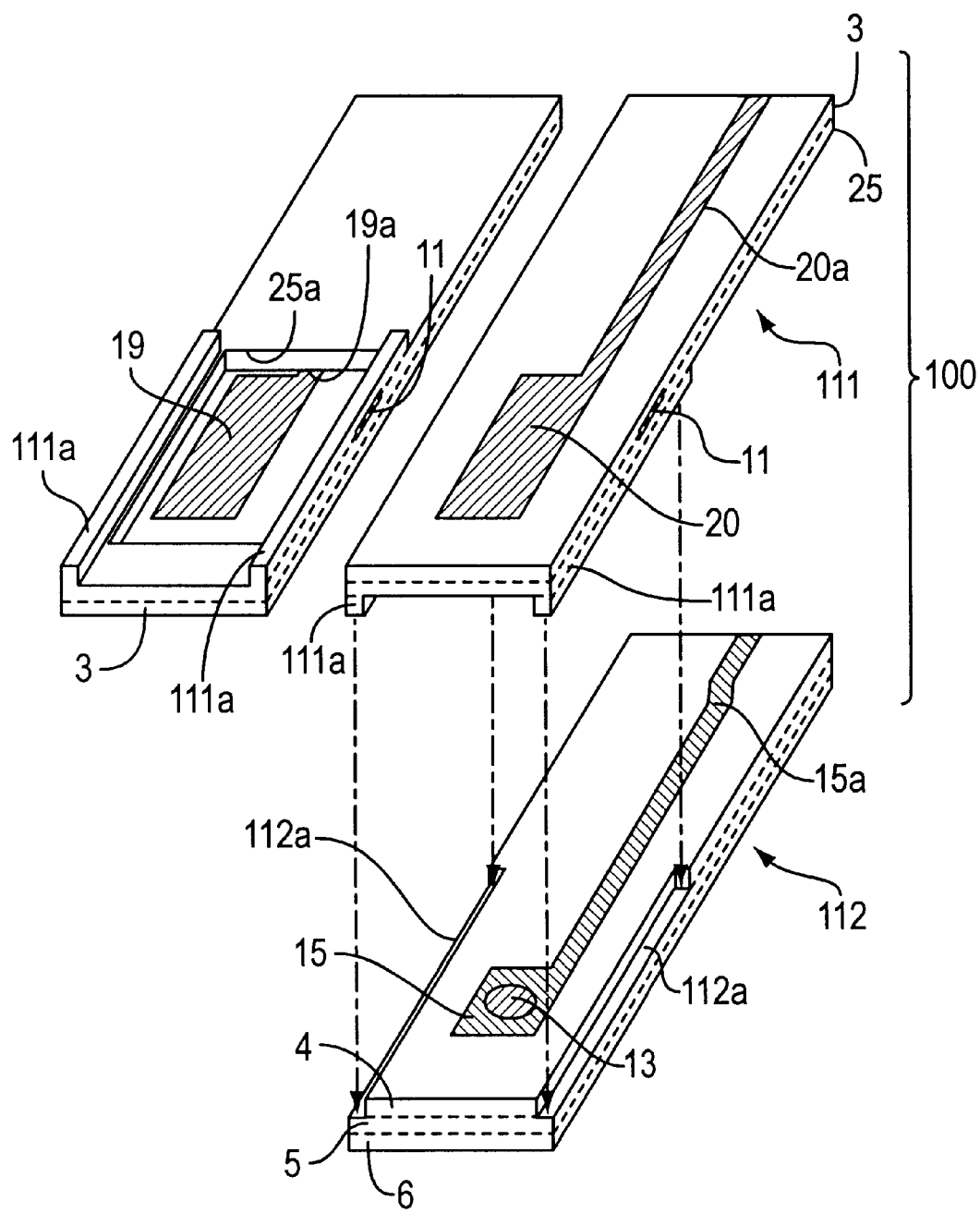
FIG. 19 is an exploded-perspective view showing the gas sensor of a second embodiment of the invention and the reverse side of the pumping cell unit.

Second Embodiment:

A gas sensor 100 of FIG. 19 shows a modification of the gas sensor shown in FIG. 1. Portions identical to those of the gas sensor 1 are denoted by the same symbols, and detailed descriptions therefor are omitted. In the following description, mainly the differences between the gas sensor 100 and the gas sensor 1 are described. In the gas sensor 100, a spacer 25 similar to that shown in FIG. 3(b) is integrated with the first pumping element 3. Thus, the first processing space is formed by means of a space 25a of the spacer section 25. The entire sensor 100 is divided into two at an interface between the spacer 25 and the oxygen concentration cell element 4. Thus, a pumping cell unit 111 is formed including the first pumping element 3, and a sensor cell unit 112 is formed including the oxygen concentration cell element 4 (oxygen concentration detection element), the second processing space (not shown in FIG. 19 but formed in the same manner as in the sensor 1 of FIG. 1), the second cell element 5, and the shield member 6. The first pumping element 3, the first cell element 4, and the spacer 25 form a main portion of the first processing space forming section, while the second cell element 5 and the shield member 6 form a main portion of the second processing space forming section.

The pumping cell unit 111 and the sensor cell unit 112 are superposed on each other such that the seventh electrode 19 faces the first electrode 15, and are joined and integrated together through use of a bonding material such as glass applied to the superposition surfaces through which they are superposed on each other. Furthermore, at the widthwise opposite sides of the superposition surface of the pumping cell unit 111 are formed rib-shaped fitting projections 111a (pump-cell-side fitting portion) that extend along the edges of the pump cell unit 111. The fitting portions 111a are fitted into the fitting depressions 112a (sensor-cell-side fitting portions) formed on the sensor cell unit 112 at corresponding portions for positioning during superposition.

Figure 20A:
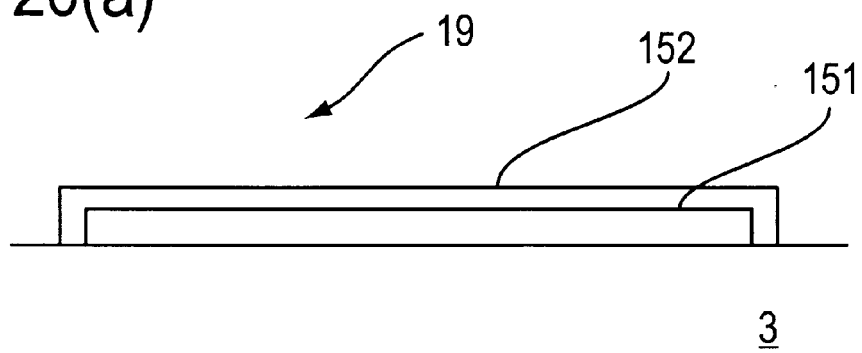
FIGS. 20(*a*), 20(*b*) and 20(*c*) are schematic diagrams showing the structure of the seventh electrode.

As shown in FIG. 20(a), the seventh electrode 19 has a two-layer structure composed of a porous main electrode layer 151 and a porous surface electrode layer 152 that forms a surface portion of the seventh electrode 19. The main electrode layer 151 is formed of Pt or a Pt—Au alloy (in the present embodiment, substantially the entire portion is formed of Pt). The surface electrode layer 152 is formed of an Au-containing metal that contains Au as a main component (in the present embodiment, substantially the entire portion is formed of Au). The first electrode 15 shown in FIG. 19 is formed of a porous metal such as porous Pt or a porous Pt—Au alloy (Au content: not greater than 1 wt. %) (in the present embodiment, substantially the entire portion is formed of Pt) as in the case of the other electrodes.

Because the surface of the porous main electrode layer 51 formed of Pt, which has a high activity of desorbing oxygen molecules, is covered with the porous surface electrode layer 152 formed of Au, which has a low catalytic activity for combustion of a combustible gas component, the catalytic activity for combustion of the combustible gas component within the first processing space can be decreased, while the activity of desorbing oxygen molecules is maintained at a sufficient level. Thus, a loss of a combustible gas component such as HC to be detected can be prevented, so that the sensor sensitivity can be increased. In the case where substantially the entire portion of the main electrode layer 151 is formed of Pt and substantially the entire portion of the surface electrode layer 152 is formed of Au, the value of {WAu/(WPt+WAu)}×100 preferably falls within the range of 2–20 wt. %, where WPt is the Pt content by weight of the seventh electrode 19, and WAu is the Au content by weight of the seventh electrode 19. When this value is less than 2 wt. %, the combustion catalytic activity of the seventh electrode 19 cannot be sufficiently decreased, with a possible result that the sensitivity of the sensor decreases. By contrast, when this value exceeds 20 wt. %, the catalytic activity of the seventh electrode 19 for desorption and recombination of oxygen molecules decreases excessively, with a possible result that the function of the oxygen pumping element 3 becomes insufficient. More preferably, the value falls within the range of 3–10 wt. %.

Figure 20B:
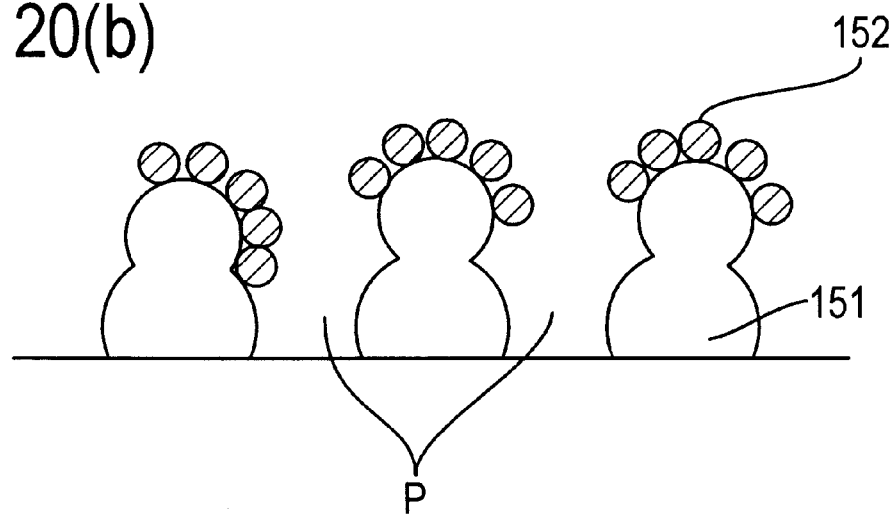
Figure 20C:
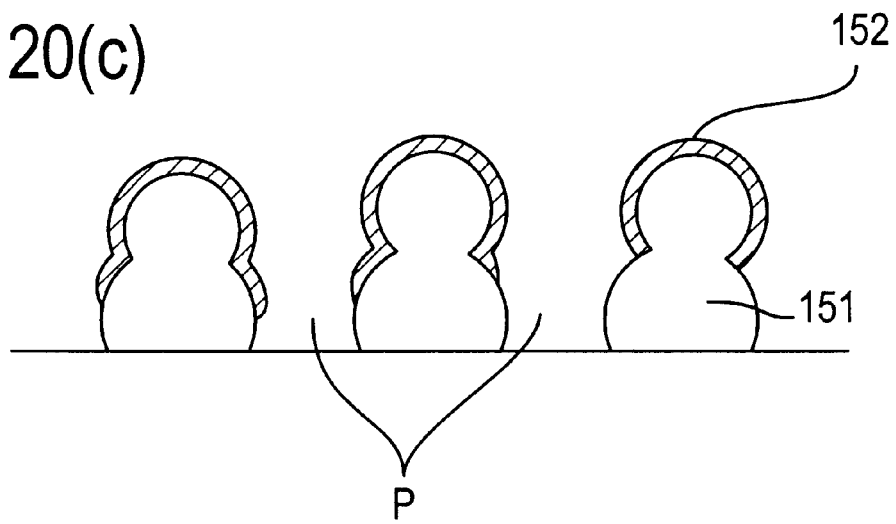

A method shown in FIG. 20(b) may be used to form the surface electrode layer 152 on the main electrode layer 151. That is, a paste containing particles of a material for the surface electrode layer 152 is applied onto the fired main electrode layer 151, and is then fired at a temperature lower that that for the firing of the main electrode layer 151. Alternatively, as shown in FIG. 20(c), the surface electrode layer 152 may be formed using vapor-phase film formation such as vacuum deposition or sputtering. As shown in FIGS. 20 (b) and (c), because many voids are formed in the porous main electrode layer 151 in a complex manner, the surface electrode layer 152 may not be formed such that its material fails to enter deeply into the voids P. In this case, parts of the main electrode layer 151 are not covered by the surface electrode layer 152 and remain exposed. However, because such exposed portions exhibit a strong catalytic activity for desorption and recombination of oxygen molecules, the formation of such exposed portions is rather preferable in terms of securing the function of the oxygen pumping element.

Figure 21:
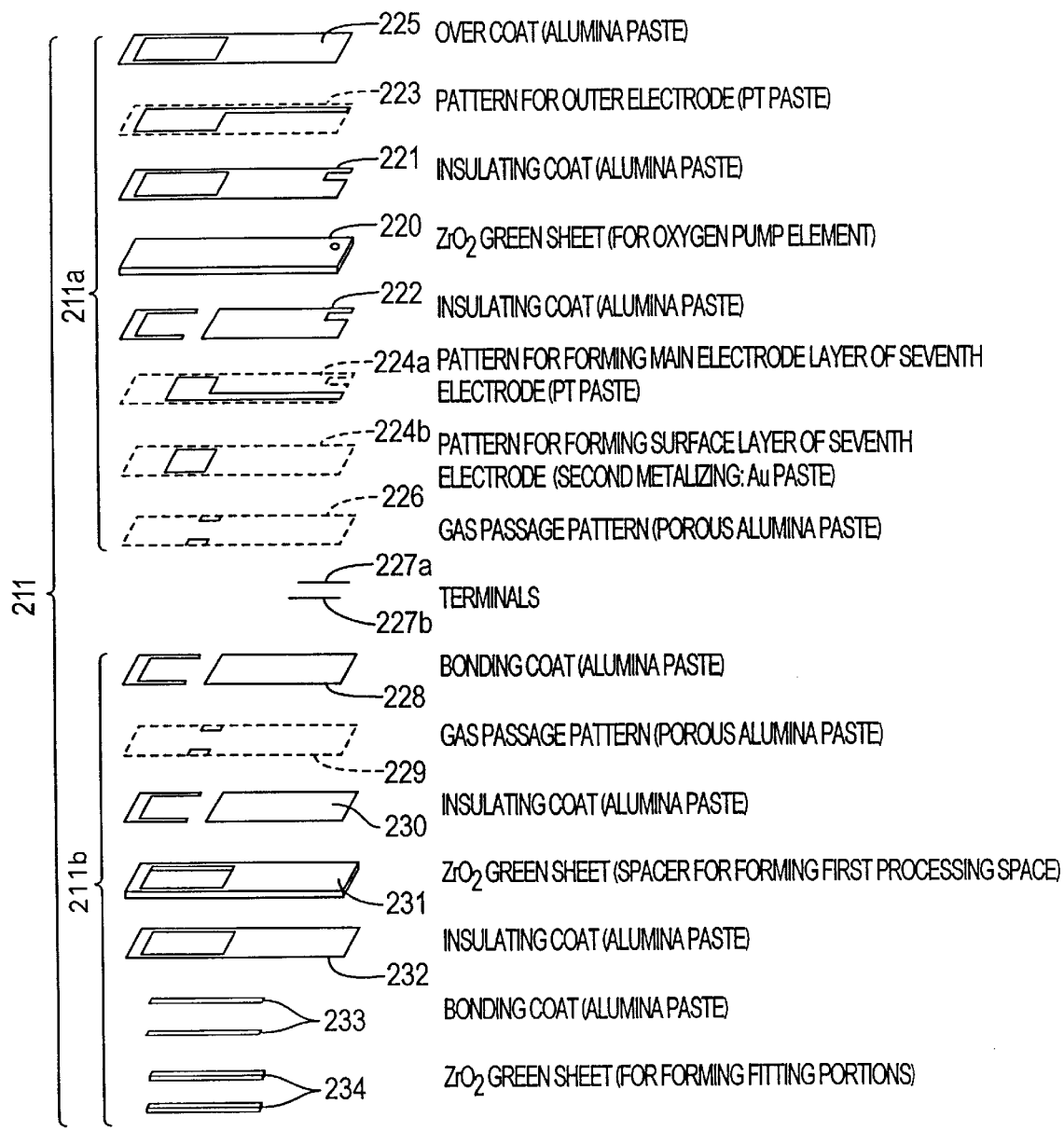
FIG. 21 is a perspective view showing a method of manufacturing the pumping cell unit of the gas sensor of FIG. 19.

An example process for manufacturing the pumping cell unit 111 and the sensor cell unit 112 shown in FIG. 19 will be described with reference to FIGS. 21 and 22. FIG. 21 shows a laminate structure of a first unfired assembly 211 used for manufacturing the pumping cell unit 111. The first unfired assembly 211 includes a first portion 211a and a second portion 211b. The first portion 211a is mainly composed of a $ZrO_2$ green sheet (hereinafter also referred to as a green sheet) 220, which will become the first pumping element 3. The second portion 211b is mainly composed of a green sheet 231, which will serve as the spacer 25. The green sheet is formed by sheeting a kneaded mixture of a $ZrO_2$ powder, a forming aid such as an organic binder, and an organic solvent.

In the first portion 211a, by using an $Al_2O_3$ paste or the like, insulating coats (insulating layer patterns) 221 and 222 for insulating the leads 20a and 19a from the first pumping element 3 are formed on the corresponding surfaces of the green sheet 220 in regions other than those corresponding to the electrodes 20 and 19 (hereinafter, for reference numerals or symbols see also FIG. 1, as needed, in addition to FIG. 19). After the insulating coats 221 and 222 are formed, electrode patterns 223 and 224a for forming the electrodes 20 and 19 (only a main electrode layer 151 for the electrode 19 (FIG. 20)) and the leads 20a and 19a are formed by printing using a Pt paste or the like. A pattern 226 of porous alumina paste or the like, which will serve as a first gas passage 11, is provided on the pattern 224b. A protective over coat 225 is formed on the electrode pattern 223, which will serve as the outer electrode 20, using an $Al_2O_3$ paste or the like.

In the second portion 211b, insulating coats 230 and 232 are formed on the corresponding surfaces of the green sheet 231 in a manner similar to that used for the first portion 211a. A pattern 229, which will serve as a first gas passage 11, is formed on the insulating coat 230 using an $Al_2O_3$ paste. Green sheets 234, which will serve as fitting projections 111a, are bonded onto the insulating coat 232 using bonding coats 233 (formed from alumina paste).

The first portion 211a and the second portion 211b are bonded together using a bonding coat 228, while end portions of Pt—Rh alloy wires 227a and 227b, which will serve as terminals of the electrodes 20 and 19, are sandwiched between the portions 211a and 211b. The thus-obtained first unfired assembly 211 is fired to obtain a pumping cell unit in which a surface electrode layer 152 (FIG. 20) of the seventh electrode 19 is not yet formed. Then, as shown in FIG. 21, by using an Au paste, a pattern 224b is printed on the fired main electrode layer at the corresponding position, followed by secondary metallization. In the secondary metallization, the printed pattern 224b is fired at a temperature (for example, 850° C. to 1000° C.) lower than a ceramics firing temperature. Thus, the multilayered fourth electrode 19 is formed, to thereby complete the pumping cell unit 111.

Figure 22:
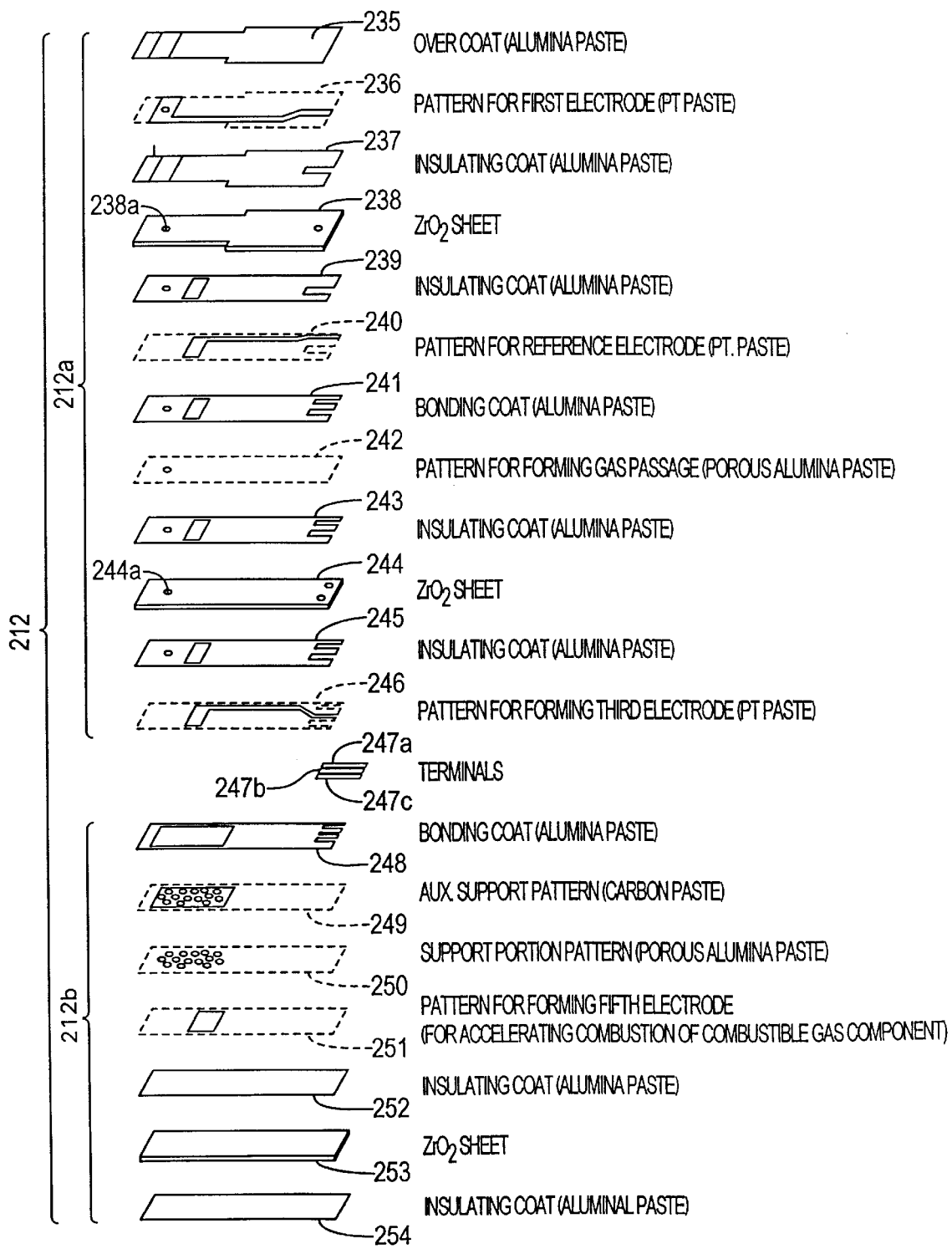
FIG. 22 is a perspective view showing a method of manufacturing the sensor cell unit of the gas sensor of FIG. 19.

FIG. 22 shows a laminate structure of a second unfired assembly 212 used for manufacturing the sensor cell unit 112. The second unfired assembly 212 includes a first portion 212a and a second portion 212b. The first portion 212a is mainly composed of a green sheet 238, which will serve as a main portion of the first cell element 4, and a green sheet 244, which will serve as a main portion of the second cell element 5. The second portion 212b is mainly composed of a green sheet 253, which will serve as the shield member 6.

In the first portion 212a, insulating coats (insulating layer patterns) 237 and 239 for insulating the leads 15a and 14a from the first cell element 4 are formed on the corresponding surfaces of the green sheet 238 in regions other than those corresponding to the electrodes 15 and 14 (hereinafter, for reference numerals or symbols see also FIG. 1, as needed, in addition to FIG. 19). After the insulating coats 237 and 239 are formed, electrode patterns 236 and 240 for forming the electrodes 15 and 14 and the leads 15a and 14a are formed by printing using a Pt paste or the like. Insulating coats 243 and 245 are formed on the corresponding surfaces of the green sheet 244. An electrode pattern 246 for forming the electrode 16 and the lead 16a is formed on the insulating coat 245. The thus-processed green sheets 238 and 244 are bonded together using a bonding coat 241. Through-holes 238a and 244a for forming the second gas passage 13 are formed in the green sheets 238 and 244. Printing of a pattern 242 causes the through-holes 238a and 244a to be filled with $Al_2O_3$ paste. Cuts, which will serve as fitting depressions 112a (FIG. 19), are formed in the green sheet 238 at widthwise edge portions. A protective over coat 235 is formed on the electrode pattern 236, which will serve as the outer electrode 20, using an $Al_2O_3$ paste or the like.

In the second portion 212b, insulating coats 252 and 254 are formed on the corresponding surfaces of the green sheet 253. A pattern 251 for forming a porous sintered metal layer for accelerating combustion of a combustible gas component is formed on the insulating coat 252 by printing using a Pt paste or the like (the pattern 251 may be omitted). A support portion pattern 250 and an auxiliary support pattern 249 are formed above the insulating coat 252 in order to form the second processing space 10 in a manner similar to that shown in FIG. 4.

The first portion 212a and the second portion 212b are bonded together using a bonding coat 248, while end portions of Pt—Rh alloy wires 247a, 247b and 247c, which will serve as terminals of the electrodes 15, 14 and 16, are sandwiched between the portions 212a and 212b. The thus-obtained second unfired assembly 212 is fired to obtain the sensor cell unit 112 shown in FIG. 19.

EXAMPLES

Example 1

In the gas sensor 1 shown in FIG. 1, the elements 3 to 5 and the shield member 6 were formed of $ZrO_2$ solid electrolyte which contained $Y_2O_3$ in an amount of 5% by weight. Among the porous electrodes 14 to 16, 19 and 20, the electrodes 15 and 16 were formed of a Pt-1% by weight of Au alloy, and other electrodes were formed of Pt. The first processing space 9 and the second processing space 10 had a height of 0.02 mm, a width of 2.2 mm, and a length of 7 mm. The sensor 1 was incorporated into the gas sensor system 50 of FIG. 6. The test gas was composed of oxygen (7%), water vapor (10%), carbon dioxide (10%), methane as a combustible gas component (0 to 500 ppmc) and nitrogen (balance). The sensor 1 was held in the test gas and heated by the heaters 2 and 8 so as to heat the elements 3 to 5 to a temperature of 650° C.

Figure 12:
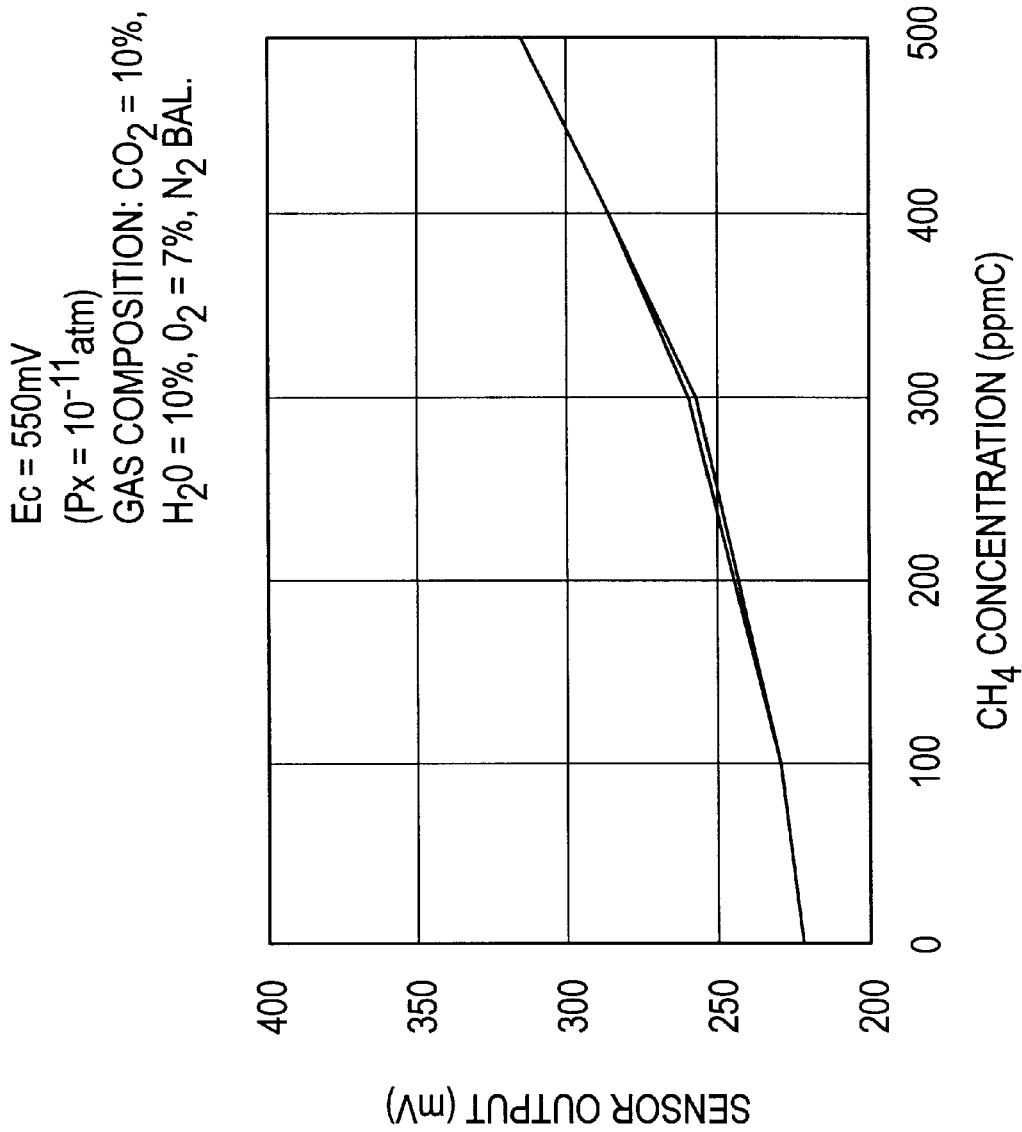
FIG. 12 is a graph showing the methane concentration dependence of the sensor output obtained in Example 1 in which the gas sensor of a present invention was used.

The target electromotive force EC of the first cell element 4 was set to a value (approximately 550 mV) such that the target oxygen concentration of the first processing space 9 was $10_{-11}$ atm. The sensor system 50 was operated under these conditions. The concentration cell electromotive force of the second cell element 5 was examined to see how it varied with the methane concentration of the test gas. The result is shown in FIG. 12. As seen from FIG. 12, the sensor output of the gas sensor 1 greatly changes with the methane concentration, indicating that the sensor 1 exhibits good sensitivity toward methane.

Figure 13:
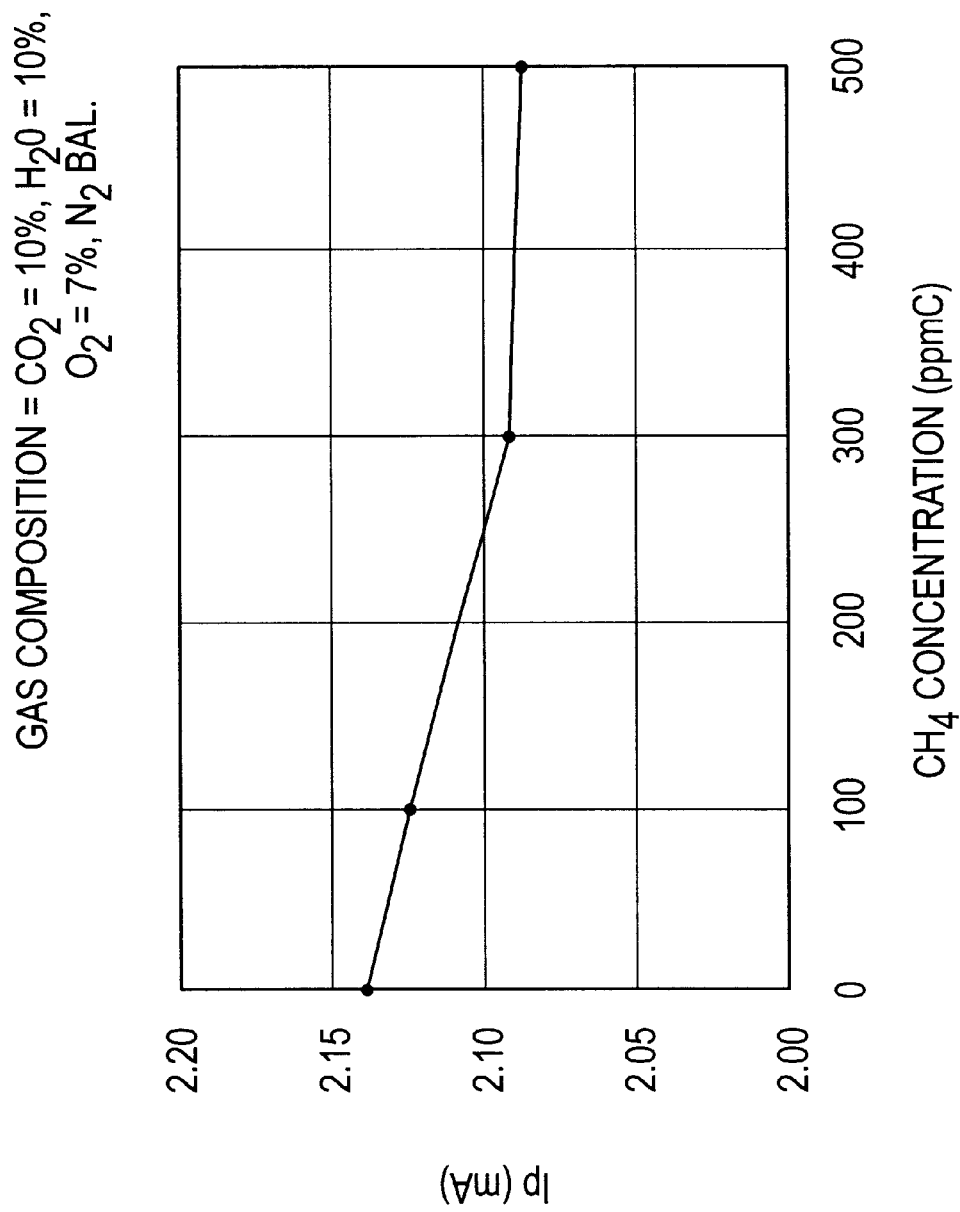
FIG. 13 is a graph showing methane concentration as a function of the pumping current of the first pumping element.

FIG. 13 shows the relationship between methane concentration and the pumping current $I_p$ of the first pumping element 3. As seen from FIG. 13, the pumping current $I_p$ decreases as the methane concentration increases. This indicates that at the above setting of the oxygen concentration of the first processing space 9, a portion of the methane component is burned. Specifically, as the methane concentration increases, the amount of burned methane increases; thus, conceivably, the amount of oxygen pumped out by the first pumping element 3 in order to maintain the target oxygen concentration, i.e., the pumping current $I_p$, decreases.

Figure 14:
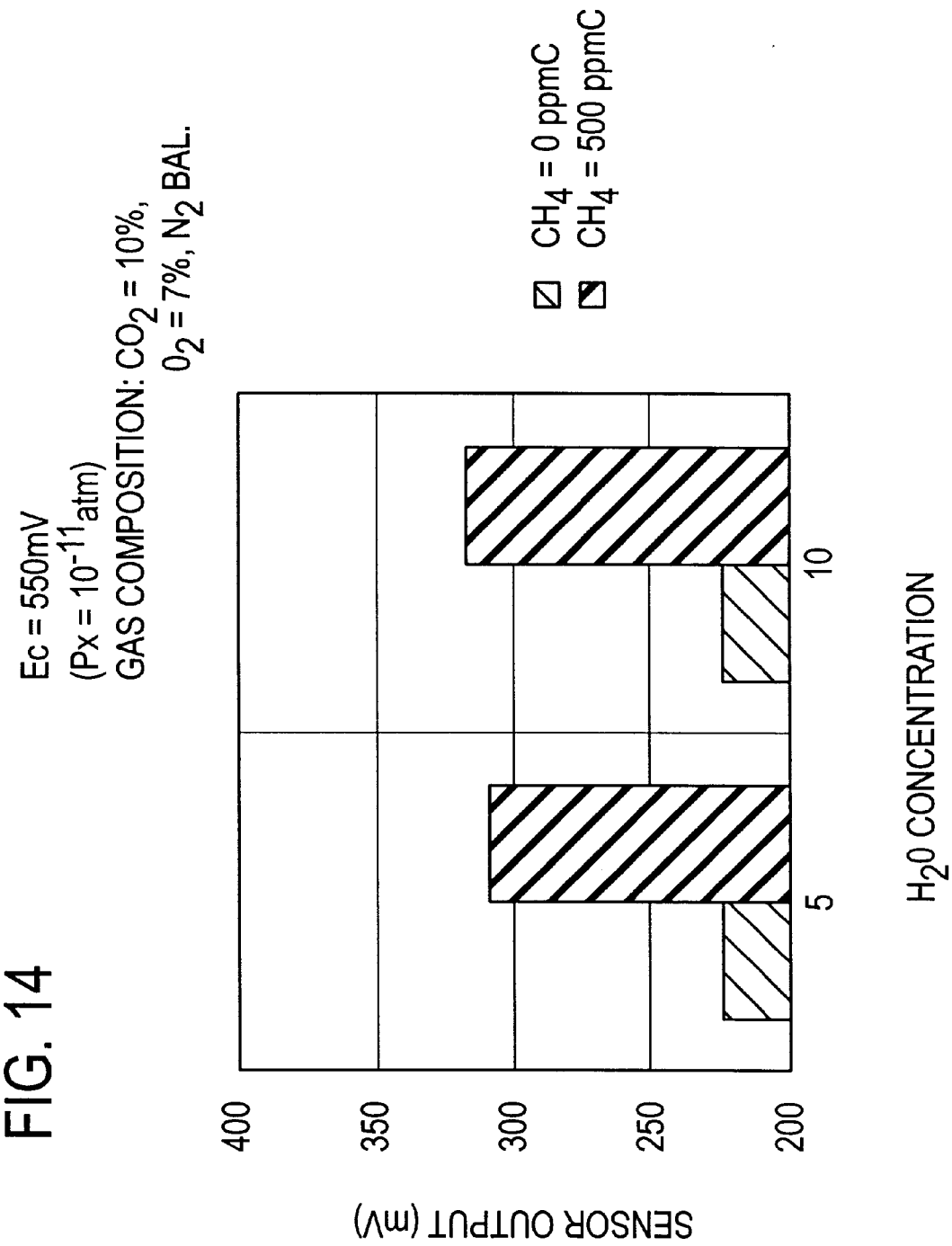
FIG. 14 is a graph showing the influence of water vapor concentration on the sensor output.
Figure 15:
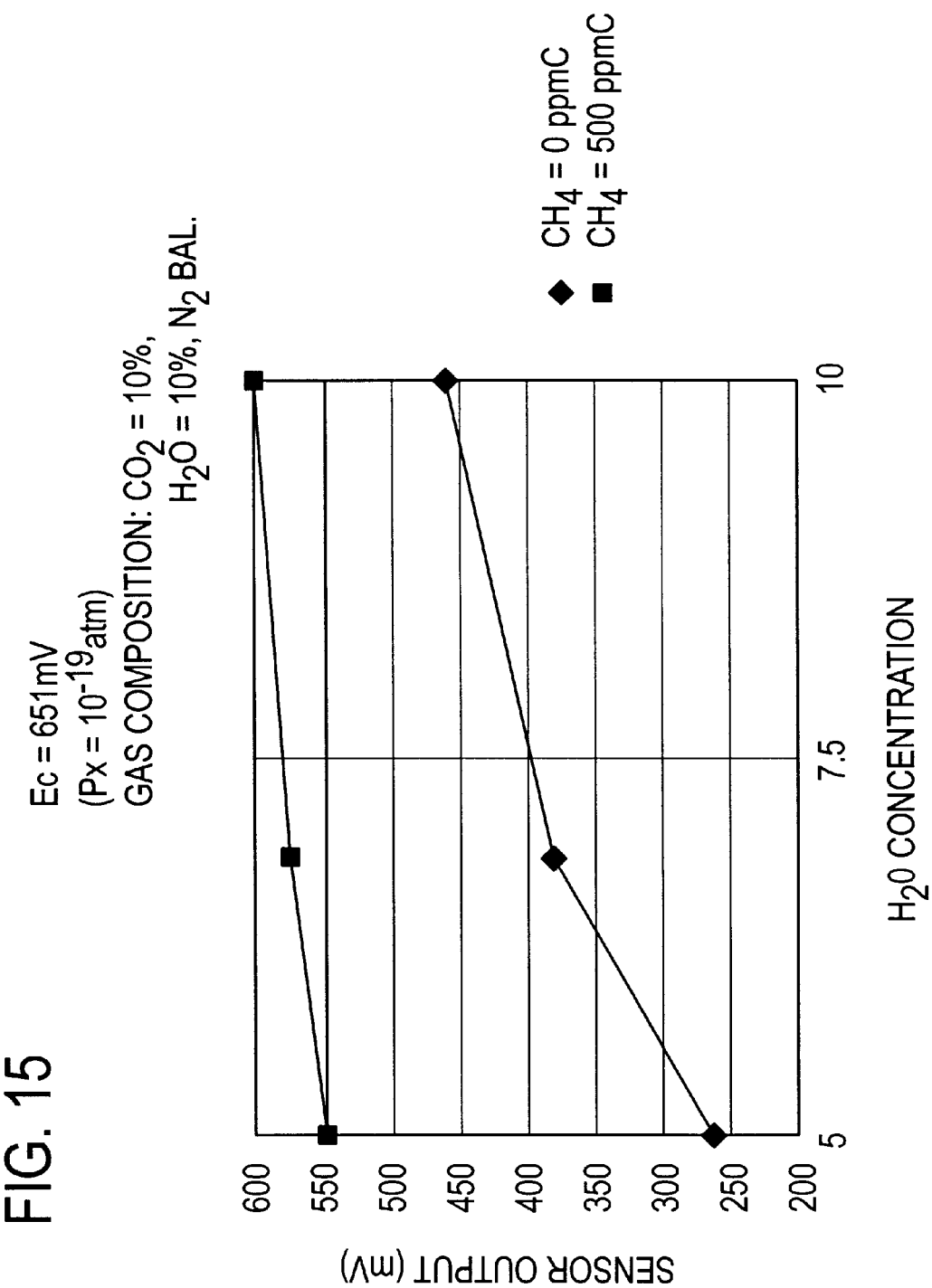
FIG. 15 is a graph showing the influence of water vapor concentration on the sensor output in the Comparative Example.

An experiment similar to that described above was conducted in a state in which the methane concentration was either 0 ppmc or 500 ppmc, the water vapor concentration was either 5% or 10%, and the concentrations of other gas components were the same as described above. The result is shown in FIG. 14. Specifically, the sensor output corresponding to either methane concentration remained almost unchanged for a water vapor concentration of 5% and 10%. This indicates that in the gas sensor 1, decomposition of water vapor is hardly initiated during measurement, and thus a stable methane concentration is obtained regardless of the water vapor concentration. As a Comparative Example, the target electromotive force EC of the first cell element 4 was set to a value (approximately 651 mV) such that the target oxygen concentration of the first processing space 9 was $10^{-13}$ atm. In this state, an experiment was conducted in a manner similar to that of the above-described experiment. The result is shown in FIG. 15. As seen from FIG. 15, the sensor output was significantly influenced by the water vapor concentration.

Example 2

Figure 17:
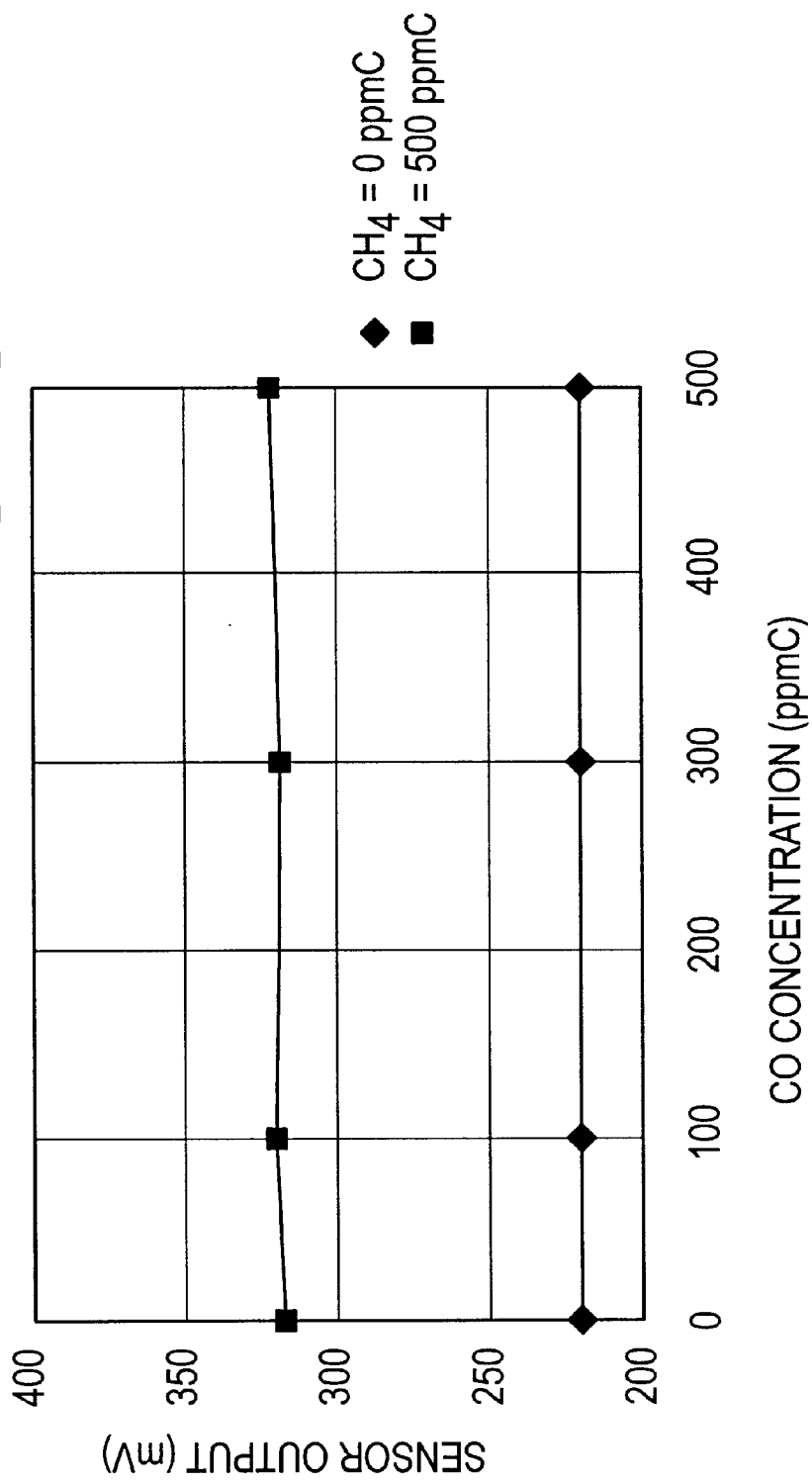
FIG. 17 is a graph showing CO concentration as a function of the sensor output obtained in Example 2 in which a gas sensor of the present invention was used.
Figure 18:
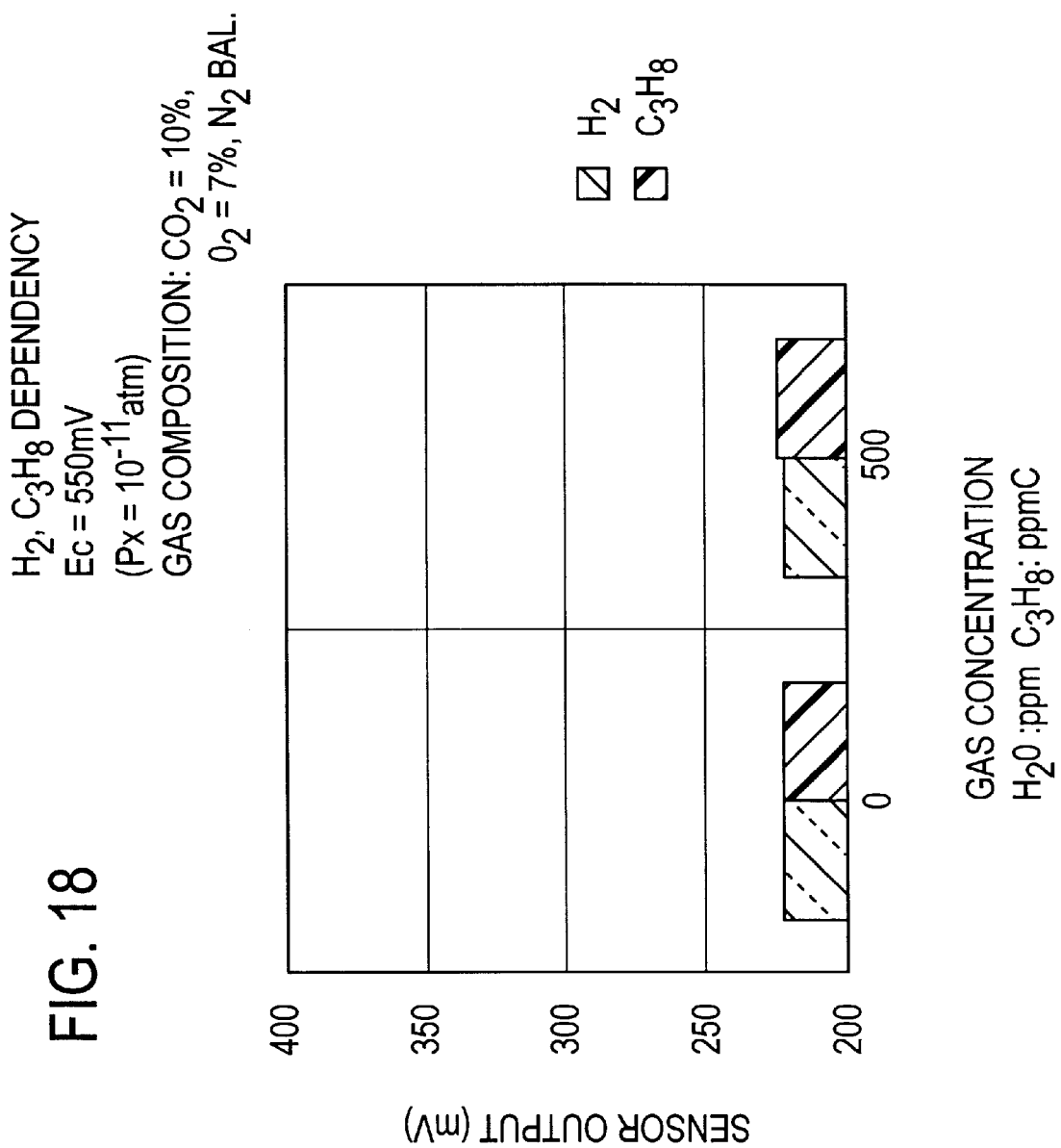
FIG. 18 is a graph showing the effect of hydrogen concentration and propane concentration on the sensor output.

Another experiment was conducted in a sate in which the same exhaust sensor 1 as used in Example 1 was built in the exhaust gas sensor system 50 of FIG. 6. In this experiment, the test gas was composed of methane (0 ppmc or 500 ppmc), CO (0–500 ppmc), oxygen (7%), water vapor (10%), carbon dioxide (10%) and nitrogen (balance). The exhaust sensor 1 was held in the test gas and heated by heaters 2 and 8 so as to heat the elements 3 to 5 to a temperature of 650° C. The target electromotive force EC of the first cell element 4 was set to a value (about 550 mV) such that the target oxygen concentration of the first processing space 9 was $10^{-11}$ atm. The sensor system 50 was operated under these conditions, and the concentration cell electromotive force of the second cell element 5 was measured as a sensor output. The result is shown in FIG. 17. As seen from FIG. 17, the sensor output corresponding to each methane concentration remained almost unchanged for any CO concentration. This demonstrates that the exhaust gas sensor 1 of the present invention stabily provides a methane concentration detection output regardless of the CO concentration. FIG. 18 shows the result of a similar experiment which was performed using test gases each of which contained hydrogen (0 ppm or 500 ppm) or propane ((0 ppm or 500 ppm) instead of methane and which also contained oxygen (7%), water vapor (10%), carbon dioxide (10%) and nitrogen (balance). The result of the experiment is shown in FIG. 18. From these results, it is seen that when a test gas does not contain methane gas, the sensor output is small and remains almost unchanged regardless of the hydrogen concentration or the propane concentration. The above-described result demonstrates that the exhaust gas sensor 1 of the present invention has excellent selectivity for detection of methane.

Example 3

In the gas sensor 100 shown in FIG. 19 (for reference numerals or symbols see also FIG. 2), the porous electrodes 14 to 16 and 20 were formed using a Pt—Au (1% by weight) alloy. The seventh electrode 19 was a two-layered electrode composed of the main electrode layer 151 (FIG. 20) and the surface electrode layer 152. The main electrode layer 151 was integrally formed with the pumping cell unit 111 using a Pt—Au (1% by weight) alloy by firing. Au paste was applied onto the main electrode layer 151, followed by secondary firing (at 900° C.) to thereby form the surface electrode layer 152. As in the case of Example 1, the first processing space 9 and the second processing space 10 each had a height of 0.02 mm, a width of 22 mm and a length of 7 mm. A section was taken across the thickness of the seventh electrode 19. The composition of the section was analyzed using an Electron Probe Micro Analyzer (EPMA; energy diffusion system). As a result, the Au content was found to be about 4.1% by weight when the total content of Au and Pt in the main electrode portion was taken as 100% by weight. It was confirmed that a surface electrode layer 152 mainly composed of Au was formed in a surface layer region of the main electrode portion.

The sensor 100 was incorporated into the gas sensor system 50 of FIG. 6. The sensor 100 was held in a test gas composed of oxygen (7%), water vapor (10%), carbon dioxide (10%), nitrogen monoxide (500 ppm), methane (200 ppmc) serving as a combustible gas component and nitrogen (balance). The sensor 100 was heated using heaters 2 and 8 (FIG. 1) so as to heat the elements 3 to 5 to a temperature of 750° C. In the gas sensor 100, the target electromotive force EC of the first oxygen concentration cell element 4 was set to a value (about 550 mV) such that the target oxygen concentration $P_x$ of the first processing space 9 was $10^{-11}$ atm. The sensor system 50 was operated under these conditions to examine how the electromotive force E of the second oxygen concentration cell element 5 varies with the methane concentration. The test revealed that the electromotive force E corresponding to a methane concentration of 200 ppmc in the gas sensor 100 was about 350 mV, which is larger than the value of about 240 mV observed with the sensor of Example 1. A conceivable reason for such an improvement in sensor sensitivity is that the above-described two-layered structure of the seventh electrode 19 facilitates combustion of methane to thereby reduce a loss associated with combustion of methane within the first processing space 9.

Figure 23C:
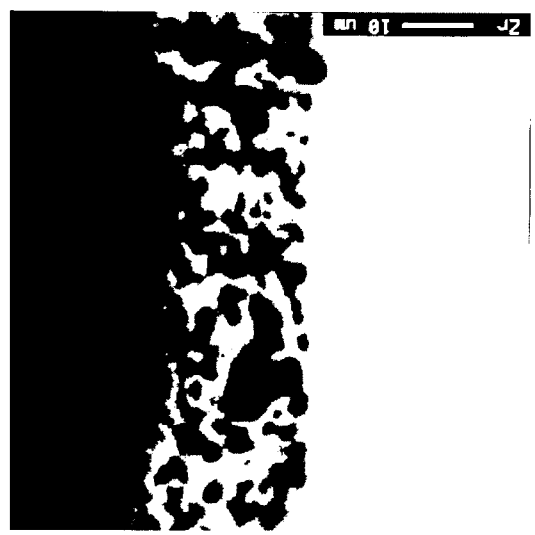
FIGS. 23(*a*), 23(*b*) and 23(*c*) are EPMA characteristic-X-ray images of Pr, Au and Zr of a cross section of the seventh electrode of the sensor used in Example 3 (before aging).
Figure 23B:
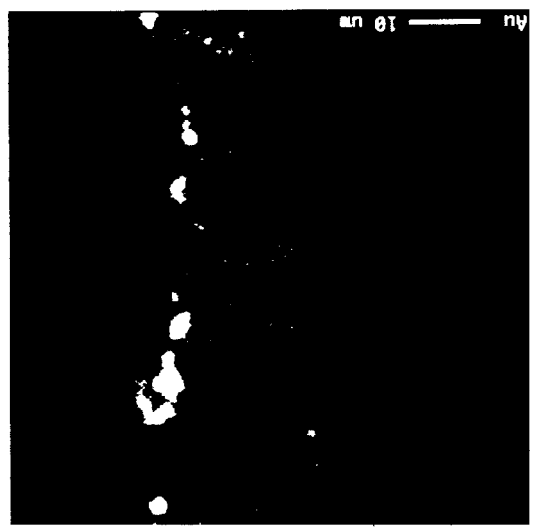
Figure 23A:
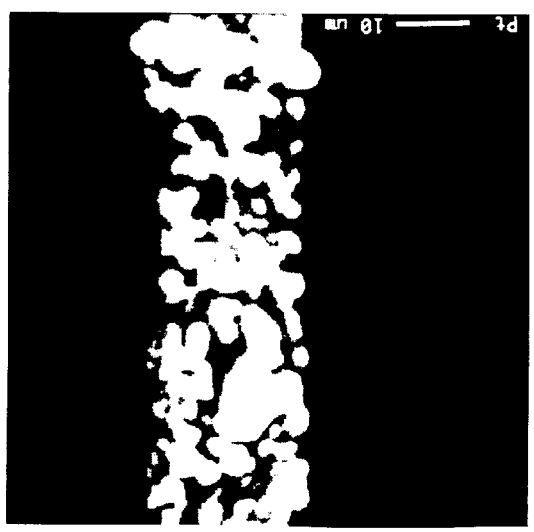

A section of the seventh electrode which was not used yet after secondary firing was examined using EPMA attached to an SEM. FIG. 23 shows characteristic X-ray images (about 1000 magnifications) of the section corresponding to Pt (FIG. 23(a)), Au (FIG. 23(b)) and Zr (FIG. 23(c)). In the images shown in FIG. 23, a brighter portion indicates a higher characteristic X-ray intensity (i.e., element concentration). As seen by comparing FIG. 23(a) and FIG. 23(c), a porous main electrode layer of Pt is formed as thick as about 20 μm on a solid electrolyte layer mainly composed of $ZrO_2$. In order to improve the bonding strength of the electrode by reducing the difference in thermal expansion coefficient between the porous electrode and the solid electrolyte layer, Pt paste blended with $ZrO_2$ powder was used as an electrode material. Thus, a region of distribution associated with a characteristic X-ray of Zr was observed in the main electrode layer. As seen by comparing FIG. 23(a) and FIG. 23(b), a surface electrode layer mainly composed of Au was formed in an outermost surface layer portion of the main electrode layer. Notably, a thin dispersion of a characteristic X-ray of Au was observed in a region corresponding to the main electrode layer. A conceivable reason is that Au had diffused from the surface electrode layer side to the main electrode layer side during secondary firing.

Figure 24C:
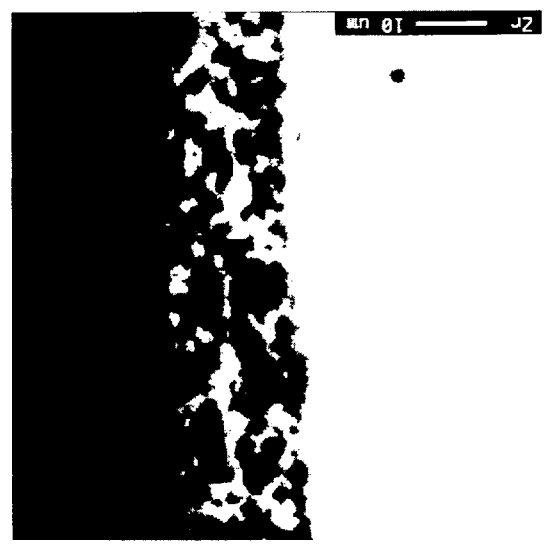
FIGS. 24(*a*), 24(*b*) and 24(*c*) are EPMA characteristic-X-ray images of Pr, Au and Zr of a cross section of the seventh electrode of the sensor used in Example 3 (after aging).
Figure 24B:
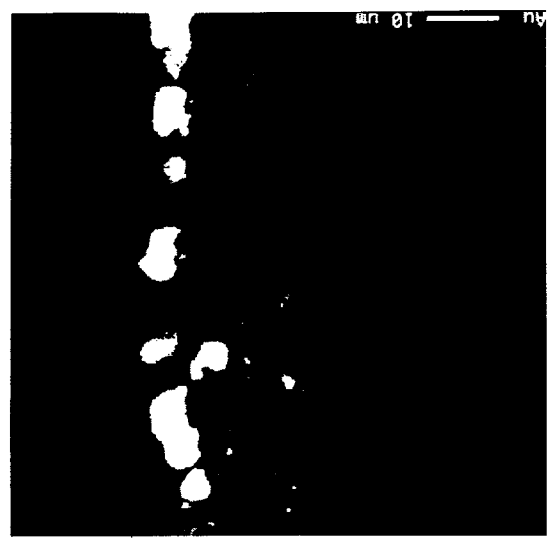
Figure 24A:
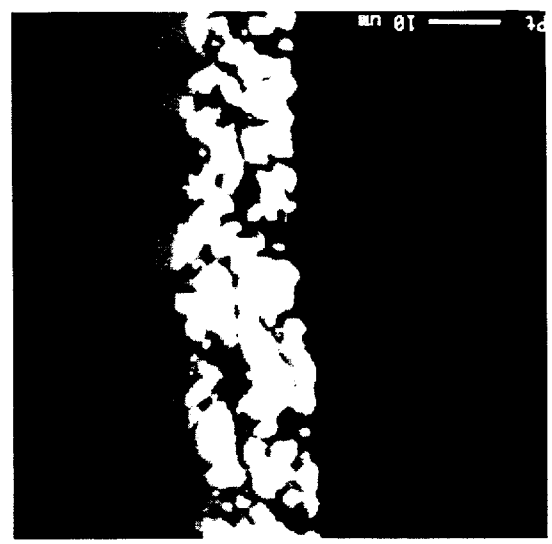

Next, the sensor was aged for 500 hours at 780° C. in the atmosphere. Subsequently, the section of the seventh electrode was examined using EPMA. FIG. 24 shows characteristic X-ray images (about 1000 magnifications) of the section corresponding to Pt (FIG. 24(a)), Au (FIG. 24(b)) and Zr (FIG. 24(c)). As compared to FIG. 23, the surface electrode layer region having a high Au concentration was wider, and the Pt concentration of the region was higher. Acceding to an Au—Pt equilibrium phase diagram, at 780° C., the solid-solution limit of Pt on the Au side was as high as about 20% by weight, while the solid-solution limit of Au on the Pt side was as low as about 5% by weight. In the main electrode layer, secondary firing most likely caused an increase in the Au concentration in the vicinity of the interface with the surface electrode layer to near a saturation concentration in Pt. Accordingly, the above-described aging is considered to have caused the following tendency: diffusion of Au from the surface electrode layer side to the main electrode layer side is relatively difficult, while diffusion of Pt from the main electrode layer to the surface electrode layer side progresses relatively easily.

As a result, diffusion of Pt to the surface electrode layer side is considered to have advanced having priority over diffusion of Au to the main electrode layer side, resulting in expansion of the surface electrode layer region. As a result of this aging, the Pt concentration of the surface electrode layer increased to about the solid-solution limit of Pt in Au (for example, 20% by weight at 780° C.). However, a Pt concentration up to this level still allows for the effect of suppressing the combustion-related catalytic activity by means of the surface electrode layer. Also, a small time-course variation in Pt concentration of the surface electrode layer while the sensor is being used may advantageously improve the time-course stability of the sensor characteristics (for example, the offset electromotive force of the oxygen concentration cell element). In this case, it is desirable to positively age the sensor in the above manner before shipment so as to sufficiently diffuse Pt to the surface electrode layer side.

Example 4

In the gas sensor 1 shown in FIG. 10, the elements 3 to 5 and 7 were formed using a $ZrO_2$ solid electrolyte containing $Y_2O_3$ in an amount of 5% by weight. The porous electrodes 14 to 18 and 20 were formed using a Pt—Au (1% by weight) alloy. The seventh electrode 19 was a two-layered electrode composed of the main electrode layer 151 (FIG. 20) and the surface electrode layer 152. The main electrode layer 151 was integrally formed with the pumping cell unit 111 using a Pt—Au (1% by weight) alloy and by firing. Au paste was applied to the main electrode layer 151, followed by secondary firing (at 900° C.) to thereby form the surface electrode layer 152. The first processing space 9 and the second processing space 10 each had a height of 0.02 mm, a width of 22 mm and a length of 7 mm. A section was taken across the thickness of the seventh electrode 19. The composition of the section was analyzed using an Electron Probe Micro Analyzer (EPMA; energy diffusion system). As a result, the Au content was found to be about 4.1% by weight when the total content of Au and Pt in the main electrode portion was taken as 100% by weight. It was confirmed that the surface electrode layer 152 mainly composed of Au was formed in a surface layer region of the main electrode portion.

The sensor 1 was incorporated into the gas sensor system 50 of FIG. 11. The sensor 1 was held in a test gas composed of methane (200 ppmc), oxygen (1%), water vapor (3 to 15%), carbon dioxide (10%) and nitrogen (balance). The sensor 1 was heated by using the heaters 2 and 8 so as to heat the elements 3 to 5 and 7 to a temperature of 650° C. In the gas sensor 1, the target electromotive force EC of the oxygen concentration cell element 4 was set to various values (250 mV (corresponding to $10^{-5}$ atm) to 750 mV (corresponding to $10^{-15}$ atm)) such that the target oxygen concentration $P_x$ of the first processing space 9 was $10^{-15}$ atm to $10^{-5}$ atm. The sensor system 50 was operated under these conditions to measure the output current $I_d$ of the oxygen pumping element 7.

Figure 16:
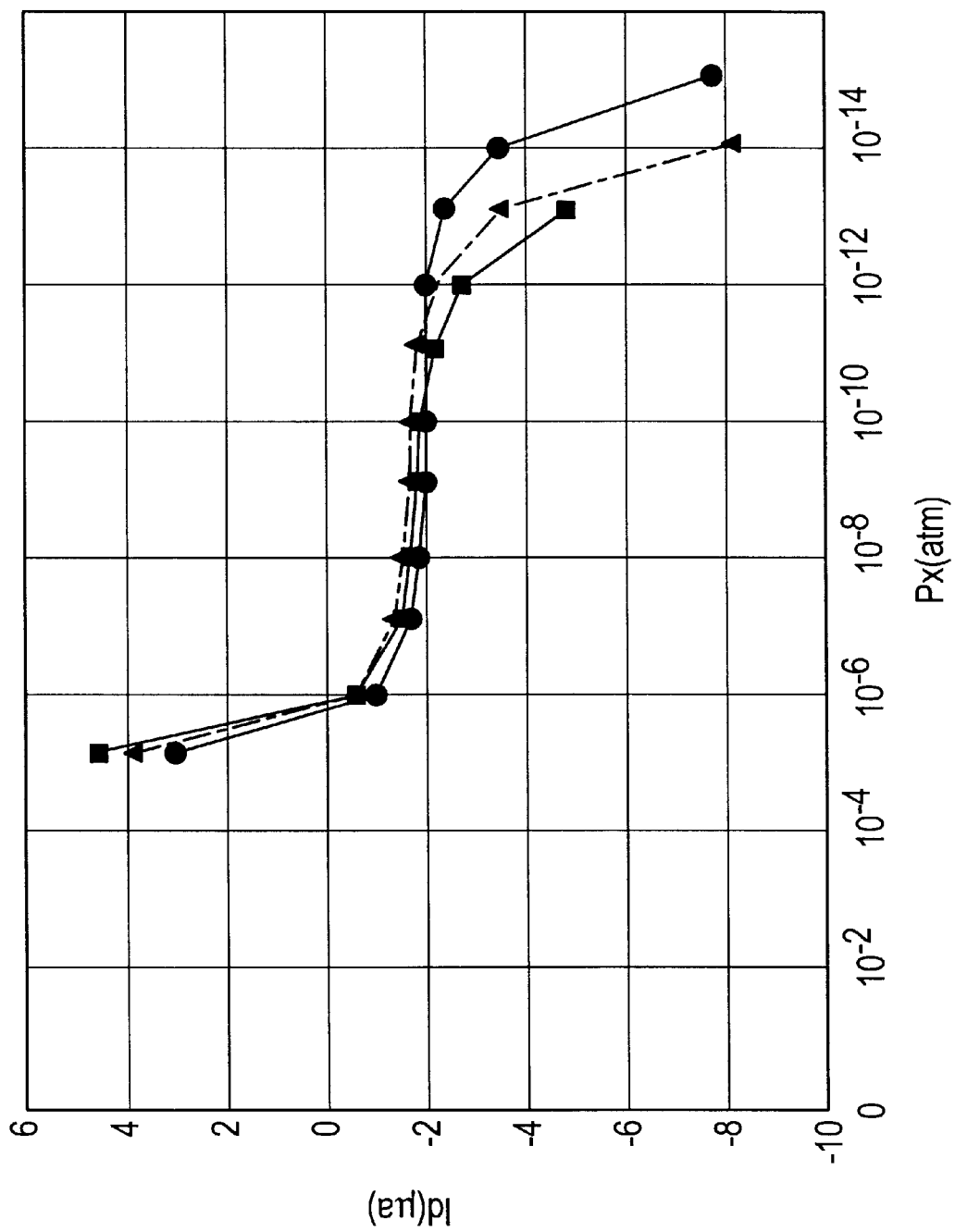
FIG. 16 is a graph showing the influence of oxygen concentration in the first processing space on the sensor sensitivity.

FIG. 16 shows the relationship between $I_d$ and $P_x$ with water vapor concentrations taken as parameters (circle: 3% of water vapor; triangle: 10% of water vapor; square: 15% of water vapor). As seen from FIG. 16, at a $P_x$ value of $10^{-12}$ atm to $10^{-6}$ atm, a substantially constant sensor output was obtained irrespective of the $P_x$ value for any of the water vapor concentrations. At a $P_x$ value of $10^{-12}$ atm or lower, $I_d$, which is expected to be constant, exhibited a sharp decrease (i.e., an increase in apparent combustible gas component concentration). It is considered that this is because a large amount of hydrogen, which is a combustible gas component, was generated as a result of water vapor decomposition. At a $P_x$ value of $10^{-6}$ atm or higher, $I_d$ exhibited a sharp increase (i.e., a decrease in apparent combustible gas component concentration). It is considered that this is because methane was burned within the first processing space, i.e., the methane concentration was reduced due to excessive oxygen concentration.

While the invention has been described in detail and with reference to specific embodiments thereof, it will be apparent to one skilled in the art that various changes and modifications can be made therein without departing from the spirit and scope thereof.

What is claimed is:

1. A gas sensor comprising:
   a first processing space and a first gas passage for introducing a measurement gas containing oxygen, water vapor and a combustible gas component into said first processing space;
   a second processing space and a second gas passage for introducing a gas contained in said first processing space into said second processing space;
   an oxygen concentration detection element for measuring the oxygen concentration of gas contained in said first processing space;
   a first oxygen pumping means for adjusting the oxygen concentration of the measurement gas introduced into said first processing space and measured by said oxygen concentration detection element within a range such that water vapor contained in the measurement gas is not substantially decomposed;
   an oxidation catalyst for accelerating combustion of a combustible gas component contained in the gas which has been introduced into said second processing space from said first processing space via the second gas passage; and
   a combustible gas component concentration information generation/output section for providing information regarding the concentration of the combustible gas component of the measurement gas, having an output which varies according to the amount of oxygen consumed by combustion of the combustible gas component contained in the gas introduced into said second processing space.

2. The gas sensor according to claim 1, wherein said oxygen concentration detection element comprises a first oxygen concentration cell element comprising an oxygen-ion conductive solid electrolyte having first and second electrodes formed on opposing surfaces thereof, said first electrode being exposed to said first processing space;
   said combustible gas component concentration information generation/output section comprising a second oxygen concentration cell element comprising an oxygen-ion conductive solid electrolyte having third and fourth electrodes formed on opposing surfaces thereof, said third electrode being exposed to said second processing space, said second oxygen concentration cell element developing an electromotive force depending on the oxygen concentration of the gas contained in said second processing space;
   said first and third electrodes each comprises a porous electrode having an oxygen molecule desorbent capability, said third electrode serving as the oxidation catalyst, and said first electrode having an oxidation-catalytic activity that is lower than that of said third electrode; and
   said combustible gas component concentration information generation/output section determining the combustible gas component concentration information based on the electromotive force developed by said second oxygen concentration cell element.

3. The gas sensor according to claim 2, comprising a first oxygen pumping means for adjusting the oxygen concentration in said first processing space as measured by said oxygen concentration detection element to a level such that part of the combustible gas component contained in the measurement gas introduced into said first processing space is burned using said first electrode as an oxidation catalyst.

4. The gas sensor according to claim 3, wherein said combustible gas component comprises hydrocarbon and another combustible gas component having a higher combustion activity than hydrocarbon, and said first oxygen pumping means adjusts the oxygen concentration in said first processing space as measured by said oxygen concentration detection element within a range such that the combustible component of the measurement gas having a higher combustion activity than hydrocarbon is burned more readily than hydrocarbon.

5. The gas sensor according to claim 4, wherein said combustible gas component having a higher combustion activity than hydrocarbon is selected from the group consisting of CO, hydrogen and ammonia.

6. The gas sensor according to claim 2, wherein said first processing space and said second processing space are arranged with a partition wall comprising an oxygen-ion conductive solid electrolyte disposed therebetween;

the second gas passage is formed in the partition wall so as to establish communication between said first processing space and said second processing space, and an oxygen reference electrode is embedded in the partition wall at the thicknesswise intermediate portion thereof;

the first electrode is formed on the partition wall adjacent to said first processing space, and the first electrode, the oxygen reference electrode and a portion of the partition wall interposed between the first electrode and the oxygen reference electrode constitute said first oxygen concentration cell element;

the third electrode is formed on the partition wall adjacent to said second processing space, and the third electrode, the oxygen reference electrode and a portion of the partition wall interposed between the third electrode and the oxygen reference electrode constitute said second oxygen concentration cell element; and said first oxygen pumping means is disposed opposite the partition wall with said first processing space disposed therebetween.

7. The gas sensor according to claim 6, wherein said second oxygen pumping element is disposed opposite the partition wall with said second processing space disposed therebetween.

8. The gas sensor according to claim 2, wherein said first oxygen pumping means comprises an oxygen-ion conductive solid electrolyte having seventh and eighth electrodes formed on opposing surfaces thereof, said seventh electrode being exposed to said first processing space;

the seventh electrode comprises:

a porous main electrode layer comprising a Pt—Au alloy or Pt; and a porous surface electrode layer covering the main electrode layer, said surface electrode layer comprising a material selected from the group consisting of a metal containing Au or Ag as a main component, a Pt—Au alloy, an Au—Pd alloy, a Pt—Ag alloy and a Pt—Ni alloy, wherein the seventh electrode has a lower oxidation-catalytic activity than the third electrode or the third and fifth electrodes.

9. The gas sensor according to claim 8, wherein the seventh electrode has a two-layer structure comprising:

a porous main electrode layer comprising a Pt—Au alloy or Pt; and a porous surface electrode layer covering the main electrode layer, said surface electrode layer comprising an Au-containing metal containing Au as a main component.

10. The gas sensor according to claim 8, wherein said first electrode has an area that is smaller than that of said seventh electrode.

11. The gas sensor according to claim 8, comprising a pumping cell unit including said first oxygen pumping means and a sensor cell unit including said oxygen concentration detection element, said pumping cell unit being arranged separately from said sensor cell unit, said second processing space and said combustible gas component concentration information generation/output section; and said pumping cell unit and said sensor cell unit being joined and integrated with each other via a bonding material.

12. The gas sensor according to claim 11, wherein said pumping cell unit comprises a pump-cell-side fitting portion unit, and said sensor cell unit comprises a sensor-cell-side fitting portion engaged with the pump-cell-side fitting portion; and said pumping cell unit and said sensor cell unit are joined and integrated with each other via engagement of the pump-cell-side fitting portion with the sensor-cell-side fitting portion.

13. A method of manufacturing a gas sensor of claim 8, said method comprising:

a substrate electrode layer forming step which comprises forming a substrate electrode pattern containing an unfired main electrode layer of material powder for the main electrode layer of the seventh electrode on an unfired solid electrolyte compact of the oxygen-ion conductive solid electrolyte layer constituting said first oxygen pumping element, and integrally firing the unfired main electrode layer with the unfired solid electrolyte compact to form on the oxygen-ion conductive solid electrolyte layer a substrate electrode layer containing the main electrode layer; and a surface electrode layer forming step which comprises forming a layer of material powder for the surface electrode layer on the substrate electrode layer, and subjecting to a secondary firing at a temperature lower than the integrally firing temperature to thereby form the surface electrode layer.

14. The manufacturing method according to claim 13, wherein said gas sensor comprises a pumping cell unit including said first oxygen pumping means and a sensor cell unit including said oxygen concentration detection element, said pumping cell unit being arranged separately from said sensor cell unit, said second processing space and said combustible gas component concentration information generation/output section; and said pumping cell unit and said sensor cell unit being joined and integrated with each other via a bonding material; and said method comprises the steps of:

firing the substrate electrode layer without forming the surface electrode layer;

carrying out said secondary firing to form the surface electrode layer on the substrate electrode layer of said pumping cell unit; and integrating said pumping cell unit with said sensor cell unit, which units have been separately manufactured through the firing steps.

15. The gas sensor according to claim 2, wherein a single same electrode serves as both of said second and fourth electrodes.

16. The gas sensor according to claim 1, wherein said oxygen concentration detection element comprises:

a first oxygen concentration cell element comprising an oxygen-ion conductive solid electrolyte having first and second electrodes formed on opposing surfaces thereof, said first electrode being exposed to said first processing space, said gas sensor further comprising:

a second oxygen concentration cell element for measuring the oxygen concentration of gas contained in said second processing space, said second oxygen concentration cell element comprising an oxygen-ion conductive solid electrolyte having third and fourth electrodes formed on opposing surfaces thereof, said third electrode being exposed to said second processing space, and wherein said combustible gas component concentration information generator/output section further comprises:

a second oxygen pumping element for pumping oxygen into said second processing space, said second oxygen pumping element comprising an oxygen-ion conductive solid electrolyte having fifth and sixth electrodes formed on opposing surfaces thereof, said fifth electrode being exposed to said second processing space, wherein said first, third and fifth electrodes each comprises a porous electrode having an oxygen molecule desorbent capability, and at least one of said third and fifth electrodes serving as the oxidation catalyst;

the first, third and fifth electrodes have an oxidation-catalytic activity such that the amount of oxygen consumed by combustion of the combustible gas component contained in said second processing space is greater than that consumed in said first processing space; and said second oxygen pumping element pumping oxygen into said second processing space to compensate for a reduction in oxygen due to combustion of the combustible gas component such that the oxygen concentration within said second processing space is substantially constant, said second oxygen pumping element outputting a pumping current or a pumping voltage when pumping oxygen into said second processing space which provides information regarding the concentration of the combustible gas component of the measurement gas.

17. The gas sensor according to claim 1, wherein said oxygen concentration detection element comprises an oxygen-ion conductive solid electrolyte having first and second electrodes formed on opposing surfaces thereof, said first electrode being exposed to said first processing space; and said first electrode comprising a porous metal comprising a Pt—Au alloy, a Pt—Ag alloy, or Pt.

18. A gas sensor comprising:

a first processing space and a first gas passage for introducing a measurement gas containing oxygen, water vapor and a combustible gas component into said first processing space;

a second processing space and a second gas passage for introducing a gas contained in said first processing space into said second processing space;

an oxygen concentration detection element for measuring the oxygen concentration of gas contained in said first processing space;

a first oxygen pumping means for adjusting the oxygen concentration of the measurement gas introduced into said first processing space and measured by said oxygen concentration detection element within a range of $10^{-12}$ atm to $10^{-6}$ atm;

an oxidation catalyst for accelerating combustion of a combustible gas component contained in the gas which has been introduced into said second processing space from said first processing space via the second gas passage after adjusting the oxygen concentration within said range; and a combustible gas component concentration information generation/output section for providing information regarding the concentration of the combustible component of the measurement gas, having an output which varies according to the amount of oxygen consumed by combustion of the combustible gas component contained in the gas introduced into said second processing space.

19. The gas sensor according to claim 18, wherein said first oxygen pumping means adjusts the oxygen concentration of the measurement gas introduced into said first processing space and measured by said oxygen concentration detection element within a range such that water vapor contained in the measurement gas is not substantially decomposed.

20. The gas sensor according to claim 18, wherein said oxygen concentration detection element comprises a first oxygen concentration cell element comprising an oxygen-ion conductive solid electrolyte having first and second electrodes formed on opposing surfaces thereof, said first electrode being exposed to said first processing space;

said combustible gas component concentration information generation/output section comprising a second oxygen concentration cell element comprising an oxygen-ion conductive solid electrolyte having third and fourth electrodes formed on opposing surfaces thereof, said third electrode being exposed said second processing space, said second oxygen concentration cell element developing an electromotive force depending on the oxygen concentration of the gas contained in said second processing space;

said first and third electrodes each comprises a porous electrode having an oxygen molecule desorbent capability, said third electrode serving as the oxidation catalyst, and said first electrode having an oxidation-catalytic activity that is lower than that of said third electrode; and said combustible gas component concentration information generation/output section determining the combustible gas component concentration information based on the electromotive force developed by said second oxygen concentration cell element.

21. The gas sensor according to claim 20, comprising a first oxygen pumping means for adjusting the oxygen concentration in said first processing space as measured by said oxygen concentration detection element to a level such that part of the combustible gas component contained in the measurement gas introduced into said first processing space is burned using said first electrode as an oxidation catalyst.

22. The gas sensor according to claim 21, wherein said combustible gas component comprises hydrocarbon and another combustible gas component having a higher combustion activity than hydrocarbon, and said first oxygen pumping means adjusts the oxygen concentration in said first processing space as measured by said oxygen concentration detection element within a range such that the combustible component of the measurement gas having a higher combustion activity than hydrocarbon is burned more readily than hydrocarbon.

23. The gas sensor according to claim 22, wherein said combustible gas component having a higher combustion activity than hydrocarbon is selected from the group consisting of CO, hydrogen and ammonia.

24. The gas sensor according to claim 20, wherein said first processing space and said second processing space are arranged with a partition wall comprising an oxygen-ion conductive solid electrolyte disposed therebetween;

the second gas passage is formed in the partition wall so as to establish communication between said first processing space and said second processing space, and an oxygen reference electrode is embedded in the partition wall at the thicknesswise intermediate portion thereof;

the first electrode is formed on the partition wall adjacent to said first processing space, and the first electrode, the oxygen reference electrode and a portion of the partition wall interposed between the first electrode and the oxygen reference electrode constitute said first oxygen concentration cell element;

the third electrode is formed on the partition wall adjacent to said second processing space, and the third electrode, the oxygen reference electrode and a portion of the partition wall interposed between the third electrode and the oxygen reference electrode constitute said second oxygen concentration cell element; and said first oxygen pumping means is disposed opposite the partition wall with said first processing space disposed therebetween.

25. The gas sensor according to claim 24, wherein said second oxygen pumping element is disposed opposite the partition wall with said second processing space disposed therebetween.

26. The gas sensor according to claim 20, wherein said first oxygen pumping element comprises an oxygen-ion conductive solid electrolyte having seventh and eighth electrodes formed on opposing surfaces thereof, said seventh electrode being exposed to said first processing space;

the seventh electrode comprises:
  a porous main electrode layer comprising a Pt—Au alloy or Pt; and
  a porous surface electrode layer covering the main electrode layer, said surface electrode layer comprising a material selected from the group consisting of a metal containing Au or Ag as a main component, a Pt—Au alloy, an Au—Pd alloy, a Pt—Ag alloy and a Pt—Ni alloy, wherein the seventh electrode has a lower oxidation-catalytic activity than the third electrode or the third and fifth electrodes.

27. The gas sensor according to claim 26, wherein the seventh electrode has a two-layer structure comprising:
  a porous main electrode layer comprising a Pt—Au alloy or Pt; and
  a porous surface electrode layer covering the main electrode layer, said surface electrode layer comprising an Au-containing metal containing Au as a main component.

28. The gas sensor according to claim 26, wherein said first electrode has an area that is smaller than that of said seventh electrode.

29. The gas sensor according to claim 26, comprising a pumping cell unit including said first oxygen pumping means and a sensor cell unit including said oxygen concentration detection element, said pumping cell unit being arranged separately from said sensor cell unit, said second processing space and said combustible gas component concentration information generation/output section; and said pumping cell unit and said sensor cell unit being joined and integrated with each other via a bonding material.

30. The gas sensor according to claim 29, wherein said pumping cell unit comprises a pump-cell-side fitting portion, unit, and said sensor cell unit comprises a sensor-cell-side fitting portion engaged with the pump-cell-side fitting portion; and
  said pumping cell unit and said sensor cell unit are joined and integrated with each other via engagement of the pump-cell-side fitting portion with the sensor-cell-side fitting portion.

31. A method of manufacturing a gas sensor of claim 26, said method comprising:
  a substrate electrode layer forming step which comprises forming a substrate electrode pattern containing an unfired main electrode layer of material powder for the main electrode layer of the seventh electrode on an unfired solid electrolyte compact of the oxygen-ion conductive solid electrolyte layer constituting said first oxygen pumping element, and integrally firing the unfired main electrode layer with the unfired solid electrolyte compact to form on the oxygen-ion conductive solid electrolyte layer a substrate electrode layer containing the main electrode layer; and
  a surface electrode layer forming step which comprises forming a layer of material powder for the surface electrode layer on the substrate electrode layer, and subjecting to a secondary firing at a temperature lower than the integrally firing temperature to thereby form the surface electrode layer.

32. The manufacturing method according to claim 31, wherein said gas sensor comprises a pumping cell unit including said first oxygen pumping means and a sensor cell unit including said oxygen concentration detection element, said pumping cell unit being arranged separately from said sensor cell unit, said second processing space and said combustible gas component concentration information generation/output section; and said pumping cell unit and said sensor cell unit being joined and integrated with each other via a bonding material; and
  said method comprises the steps of:
  firing the substrate electrode layer without forming the surface electrode layer;
  carrying out said secondary firing to form the surface electrode layer on the substrate electrode layer of said pumping cell unit; and
  integrating said pumping cell unit with said sensor cell unit, which units have been separately manufactured through the firing steps.

33. The gas sensor according to claim 20, wherein a single same electrode serves as both of said second and fourth electrodes.

34. The gas sensor according to claim 18, wherein said oxygen concentration detection element comprises:
  a first oxygen concentration cell element comprising an oxygen-ion conductive solid electrolyte having first and second electrodes formed on opposing surfaces thereof, said first electrode being exposed to said first processing space, said gas sensor further comprising:
  a second oxygen concentration cell element for measuring the oxygen concentration of gas contained in said second processing space, said second oxygen concentration cell element comprising an oxygen-ion conductive solid electrolyte having third and fourth electrodes formed on opposing surfaces thereof, said third electrode being exposed to said second processing space, and wherein said combustible gas component concentration information generator/output section further comprises:
  a second oxygen pumping element for pumping oxygen into said second processing space, said second oxygen pumping element comprising an oxygen-ion conductive solid electrolyte having fifth and sixth electrodes formed on opposing surfaces thereof, said fifth electrode being exposed to said second processing space, wherein
  said first, third and fifth electrodes each comprises a porous electrode having an oxygen molecule desorbent capability, and at least one of said third and fifth electrodes serving as the oxidation catalyst;

the first, third and fifth electrodes have an oxidation-catalytic activity such that the amount of oxygen consumed by combustion of the combustible gas component contained in said second processing space is greater than that consumed in said first processing space; and said second oxygen pumping element pumping oxygen into said second processing space to compensate for a reduction in oxygen due to combustion of the combustible gas component such that the oxygen concentration within said second processing space is substantially constant, said second oxygen pumping element outputting a pumping current or a pumping voltage when pumping oxygen into said second processing space and which provides information regarding the concentration of the combustible gas component of the measurement gas.

35. The gas sensor according to claim 18, wherein said oxygen concentration detection element comprises an oxygen-ion conductive solid electrolyte having first and second electrodes formed on opposing surfaces thereof, said first electrode being exposed to said first processing space; and said first electrode comprising a porous metal comprising a Pt—Au alloy, a Pt—Ag alloy, or Pt.

36. A gas sensor system comprising:

a first processing space and a first gas passage for introducing a measurement gas containing oxygen, water vapor and a combustible gas component into said first processing space;

a second processing space and a second gas passage for introducing a gas contained in said first processing space into said second processing space;

an oxygen concentration detection element for measuring the oxygen concentration of gas contained in said first processing space;

a first oxygen pumping element comprising an oxygen-ion conductive solid electrolyte having electrodes formed on opposing surfaces thereof, said first oxygen pumping element pumping out oxygen from said first processing space or pumping oxygen into said first processing space;

an oxidation catalyst for accelerating combustion of a combustible gas component contained in the gas which has been introduced into said second processing space from said first processing space via the second gas passage; and a combustible gas component concentration information generation/output section for providing information regarding the concentration of the combustible gas component of the measurement gas, having an output which varies according to the amount of oxygen consumed by combustion of the combustible gas component contained in the gas introduced into said second processing space; and first oxygen pumping operation control means for controlling said first oxygen pumping element and adjusting the oxygen concentration of the measurement gas introduced into said first processing space and measured by said oxygen concentration detection element within a range such that water vapor contained in the measurement gas is not substantially decomposed.

37. The gas sensor system according to claim 36, wherein said oxygen concentration detection element comprises a first oxygen concentration cell element comprising an oxygen-ion conductive solid electrolyte having first and second electrodes formed on opposing surfaces thereof, said first electrode being exposed to said first processing space;

said combustible gas component concentration information generation/output section comprising a second oxygen concentration cell element comprising an oxygen-ion conductive solid electrolyte having third and fourth electrodes formed on opposing surfaces thereof, said third electrode being exposed to said second processing space, said second oxygen concentration cell element developing an electromotive force depending on the oxygen concentration of the gas contained in said second processing space;

said first and third electrodes each comprises a porous electrode having an oxygen molecule desorbent capability, said third electrode serving as the oxidation catalyst, and said first electrode having an oxidation-catalytic activity that is lower than that of said third electrode; and said combustible gas component concentration information generation/output section determining the combustible gas component concentration information based on the electromotive force developed by said second oxygen concentration cell element.

38. The gas sensor system according to claim 37, comprising a first oxygen pumping element for adjusting the oxygen concentration in said first processing space as measured by said oxygen concentration detection element to a level such that part of the combustible gas component contained in the measurement gas introduced into said first processing space is burned using said first electrode as an oxidation catalyst.

39. The gas sensor system according to claim 38, wherein said combustible gas component comprises hydrocarbon and another combustible gas component having a higher combustion activity than hydrocarbon, and said first oxygen pumping element adjusts the oxygen concentration in said first processing space as measured by said oxygen concentration detection element within a range such that the combustible component of the measurement gas having a higher combustion activity than hydrocarbon is burned more readily than hydrocarbon.

40. The gas sensor system according to claim 39, wherein said combustible gas component having a higher combustion activity than hydrocarbon is selected from the group consisting of CO, hydrogen and ammonia.

41. The gas sensor system according to claim 36, wherein said oxygen concentration detection element comprises:

a first oxygen concentration cell element comprising an oxygen-ion conductive solid electrolyte having first and second electrodes formed on opposing surfaces thereof, said first electrode being exposed to said first processing space, said gas sensor further comprising:

a second oxygen concentration cell element for measuring the oxygen concentration of gas contained in said second processing space, said second oxygen concentration cell element comprising an oxygen-ion conductive solid electrolyte having third and fourth electrodes formed on opposing surfaces thereof, said third electrode being exposed to said second processing space, and wherein said combustible gas component concentration information generator/output section further comprises:

a second oxygen pumping element for pumping oxygen into said second processing space, said second oxygen pumping element comprising an oxygen-ion conductive solid electrolyte having fifth and sixth electrodes formed on opposing surfaces thereof, said fifth electrode being exposed to said second processing space, wherein said first, third and fifth electrodes each comprises a porous electrode having an oxygen molecule desorbent capability, and at least one of said third and fifth electrodes serving as the oxidation catalyst;

the first, third and fifth electrodes have an oxidation-catalytic activity, such that the amount of oxygen consumed by combustion of the combustible gas component contained in said second processing space is greater than that consumed in said first processing space; and said second oxygen pumping element pumping oxygen into said second processing space to compensate for a reduction in oxygen due to combustion of the combustible gas component such that the oxygen concentration within said second processing space is substantially constant, said second oxygen pumping element outputting a pumping current or a pumping voltage when pumping oxygen into said second processing space which provides information regarding the concentration of the combustible gas component of the measurement gas.

42. A gas sensor system comprising:

a first processing space and a first gas passage for introducing a measurement gas containing oxygen, water vapor and a combustible gas component into said first processing space;

a second processing space and a second gas passage for introducing a gas contained in said first processing space into said second processing space;

an oxygen concentration detection element for measuring the oxygen concentration of gas contained in said first processing space;

a first oxygen pumping element comprising an oxygen-ion conductive solid electrolyte having electrodes formed on opposing surfaces thereof, said first oxygen pumping element pumping out oxygen from said first processing space or pumping oxygen into said first processing space;

an oxidation catalyst for accelerating combustion of a combustible gas component contained in the gas which has been introduced into said second processing space from said first processing space via the second gas passage; and a combustible gas component concentration information generation/output section for providing information regarding the concentration of the combustible component of the measurement gas, having an output which varies according to the amount of oxygen consumed by combustion of the combustible gas component contained in the gas introduced into said second processing space; and first oxygen pumping operation control means for controlling said first oxygen pumping element and adjusting the oxygen concentration of the measurement gas introduced into said first processing space and measured by said oxygen concentration detection element within a range of $10^{-12}$ atm to $10^{-6}$ atm.

43. The gas sensor system according to claim 42, wherein said first oxygen pumping operation control means controls said first oxygen pumping element so as to adjust the oxygen concentration of the measurement gas introduced into said first processing space and measured by said oxygen concentration detection element within a range such that water vapor contained in the measurement gas is not substantially decomposed.

44. The gas sensor system according to claim 42, wherein said oxygen concentration detection element comprises a first oxygen concentration cell element comprising an oxygen-ion conductive solid electrolyte and having first and second electrodes formed on opposing surfaces thereof, said first electrode being exposed to said first processing space;

said combustible gas component concentration information generation/output section comprising a second oxygen concentration cell element comprising an oxygen-ion conductive solid electrolyte having third and fourth electrodes formed on opposing surfaces thereof, said third electrode being exposed to said second processing space, said second oxygen concentration cell element developing an electromotive force depending on the oxygen concentration of the gas contained in said second processing space;

said first and third electrodes each comprises a porous electrode having an oxygen molecule desorbent capability, said third electrode serving as the oxidation catalyst, and said first electrode having an oxidation-catalytic activity that is lower than that of said third electrode; and said combustible gas component concentration information generation/output section determining combustible gas component concentration information based on the electromotive force developed by said second oxygen concentration cell element.

45. The gas sensor system according to claim 44, comprising a first oxygen pumping element for adjusting the oxygen concentration in said first processing space as measured by said oxygen concentration detection element to a level such that part of the combustible gas component contained in the measurement gas introduced into said first processing space is burned using said first electrode as an oxidation catalyst.

46. The gas sensor system according to claim 45, wherein said combustible gas component comprises hydrocarbon and another combustible gas component having a higher combustion activity than hydrocarbon, and said first oxygen pumping element adjusts the oxygen concentration in said first processing space as measured by said oxygen concentration detection element within a range such that the combustible component of the measurement gas having a higher combustion activity than hydrocarbon is burned more readily than hydrocarbon.

47. The gas sensor system according to claim 46, wherein said combustible gas component having a higher combustion than hydrocarbon is selected from the group consisting of CO, hydrogen and ammonia.

48. The gas sensor system according to claim 42, wherein said oxygen concentration detection element comprises:

a first oxygen concentration cell element comprising an oxygen-ion conductive solid electrolyte having first and second electrodes formed on opposing surfaces thereof, said first electrode being exposed to said first processing space, said gas sensor further comprising:

a second oxygen concentration cell element for measuring the oxygen concentration of gas contained in said second processing space, said second oxygen concentration cell element comprising an oxygen-ion conductive solid electrolyte having third and fourth electrodes formed on opposing surfaces thereof, said third electrode being exposed to said second processing space, and wherein said combustible gas component concentration information generator/output section further comprises:

a second oxygen pumping element for pumping oxygen into said second processing space, said second oxygen pumping element comprising an oxygen-ion conductive solid electrolyte having fifth and sixth electrodes formed on opposing surfaces thereof, said fifth electrode being exposed to said second processing space, wherein said first, third and fifth electrodes each comprises a porous electrode having an oxygen molecule desorbent capability, and at least one of said third and fifth electrodes serving as the oxidation catalyst;

the first, third and fifth electrodes have an oxidation-catalytic activity such that the amount of oxygen consumed by combustion of the combustible gas component contained in said second processing space is greater than that consumed in said first processing space; and said second oxygen pumping element pumping oxygen into said second processing space to compensate for a reduction in oxygen due to combustion of the combustible gas component such that the oxygen concentration within said second processing space is substantially constant, said second oxygen pumping element outputting a pumping current or a pumping voltage when pumping oxygen into said second processing space which provides information regarding the concentration of the combustible gas component of the measurement gas.

* * * * *